(12) United States Patent
Heaslip et al.

(10) Patent No.: US 6,539,805 B2
(45) Date of Patent: *Apr. 1, 2003

(54) LIQUID METAL FLOW CONDITION DETECTION

(75) Inventors: Lawrence J. Heaslip, Burlington (CA); James D. Dorricott, Burlington (CA)

(73) Assignee: Vesuvius Crucible Company, Wilmington, DE (US)

( * ) Notice: Subject to any disclaimer, the term of this patent is extended or adjusted under 35 U.S.C. 154(b) by 43 days.

This patent is subject to a terminal disclaimer.

(21) Appl. No.: 09/812,110

(22) Filed: Mar. 15, 2001

(65) Prior Publication Data

US 2001/0029785 A1 Oct. 18, 2001

Related U.S. Application Data

(63) Continuation-in-part of application No. 09/097,401, filed on Jun. 15, 1998, now abandoned, which is a continuation of application No. 08/745,067, filed on Nov. 7, 1996, now abandoned, which is a continuation of application No. 08/277,409, filed on Jul. 19, 1994, now Pat. No. 5,633,462.

(51) Int. Cl.[7] .............................................. G01H 11/00

(52) U.S. Cl. ........................ 73/649; 164/453; 164/150.1

(58) Field of Search ........................ 73/649, 1.83, 1.86, 73/64.53, 658, 659; 164/453, 457, 4.1, 150.1; 340/683; 137/486; 266/99; 702/34, 35, 39, 48, 56, 103

(56) References Cited

U.S. PATENT DOCUMENTS

| | | |
|---|---|---|
| 2,865,196 A | 12/1958 | Bordenave et al. ............ 73/597 |
| 3,435,664 A | 4/1969 | Harris ........................ 73/54.41 |
| 3,548,640 A | 12/1970 | Deason et al. ................. 73/590 |
| 3,623,357 A | 11/1971 | Abbotts ....................... 73/32 R |
| 3,641,550 A | 2/1972 | Lynas et al. ................... 73/583 |
| 3,654,072 A | 4/1972 | Massa .......................... 162/49 |
| 3,875,989 A | 4/1975 | Pirlet .......................... 164/4.1 |
| 3,906,780 A | 9/1975 | Baldwin ..................... 73/61.75 |
| 4,140,300 A | 2/1979 | Gruner et al. ................. 266/45 |
| 4,145,917 A | 3/1979 | Brazhinkov et al. ........ 73/64.53 |
| 4,235,095 A | 11/1980 | Lieberman ................. 73/19.03 |
| 4,240,287 A | 12/1980 | Mast et al. ................. 73/61.75 |
| 4,383,624 A | 5/1983 | Stein et al. ................... 222/600 |
| 4,398,948 A | * 8/1983 | Emoto et al. .................. 75/375 |
| 4,436,976 A | 3/1984 | Inoue ........................ 219/69.2 |
| 4,475,401 A | 10/1984 | Punia et al. ................... 73/658 |
| 4,538,451 A | 9/1985 | Reichard .................... 73/61.75 |
| 4,563,895 A | 1/1986 | Eckert ......................... 73/644 |
| 4,565,088 A | 1/1986 | Crambes ................... 73/290 V |
| 4,583,717 A | 4/1986 | Hasegawa et al. ............ 266/44 |
| 4,607,520 A | 8/1986 | Dam ......................... 73/19.03 |

(List continued on next page.)

FOREIGN PATENT DOCUMENTS

| | | |
|---|---|---|
| DE | 2637421 | 7/1977 |
| DE | 132613 | 10/1978 |
| DE | 3506426 | 11/1985 |

(List continued on next page.)

Primary Examiner—Daniel S. Larkin
Assistant Examiner—Rose M. Miller
(74) Attorney, Agent, or Firm—Handal & Morofsky

(57) ABSTRACT

An apparatus and method for detecting the condition of the flow of liquid metal in or from a teeming vessel includes one or more sensors for detecting vibration caused by a flow of liquid metal in or from the teeming vessel and for outputting a sensor signal corresponding to mechanical and acoustic vibrations detected by the sensor. A signal processor receives the sensor signal and compares the sensor signal to a reference calibration signal and outputs a comparison signal. A logic unit receives the comparison signal and outputs a status signal indicative of the condition of the flow of the liquid metal in or from the teeming vessel which can be used to stop the flow of metal. The calibration signal can be static or may be dynamically updated.

43 Claims, 12 Drawing Sheets

U.S. PATENT DOCUMENTS

| | | | |
|---|---|---|---|
| 4,635,832 A | 1/1987 | Angerer et al. | 222/590 |
| 4,646,273 A | 2/1987 | Carlson et al. | 367/32 |
| 4,870,037 A | 9/1989 | Hoggard et al. | 501/98.1 |
| 4,973,386 A | 11/1990 | Callegari et al. | 201/1 |
| 5,019,159 A | 5/1991 | Muller et al. | 75/533 |
| 5,022,266 A | 6/1991 | Cody et al. | 73/579 |
| 5,028,033 A | 7/1991 | Morioka et al. | 266/45 |
| 5,042,700 A | 8/1991 | Ardell et al. | 222/590 |
| 5,083,452 A | 1/1992 | Hope | 73/61.49 |
| 5,203,909 A | 4/1993 | Petrushka et al. | 75/375 |
| 5,251,469 A | 10/1993 | Chan | 73/1.86 |
| 5,633,462 A | 5/1997 | Heaslip et al. | 73/649 |

FOREIGN PATENT DOCUMENTS

| | | |
|---|---|---|
| GB | 22215051 | 2/1989 |
| JP | 47-23763 | 10/1972 |
| JP | 55-97846 | 7/1980 |
| JP | 57-72752 | 5/1982 |
| JP | 58-13467 | 1/1983 |
| JP | 58-13455 | 7/1983 |
| JP | 57-67910 | 10/1983 |
| JP | 60-148652 | 1/1984 |
| JP | 60-118652 | 6/1985 |
| JP | 61-144254 | 7/1986 |
| JP | 61-212465 | 9/1986 |
| JP | 61-235056 | 10/1986 |
| JP | 62-21448 | 1/1987 |
| JP | 62-263858 | 11/1987 |
| JP | 03-17215 | 3/1989 |
| JP | 03-184824 | 8/1991 |
| JP | 03-264146 | 11/1991 |
| SE | 431618 | 2/1984 |
| SU | 872016 | 5/1979 |
| SU | 1488308 | 6/1989 |

\* cited by examiner

GENERATION OF CALIBRATION SPECTRUM 41

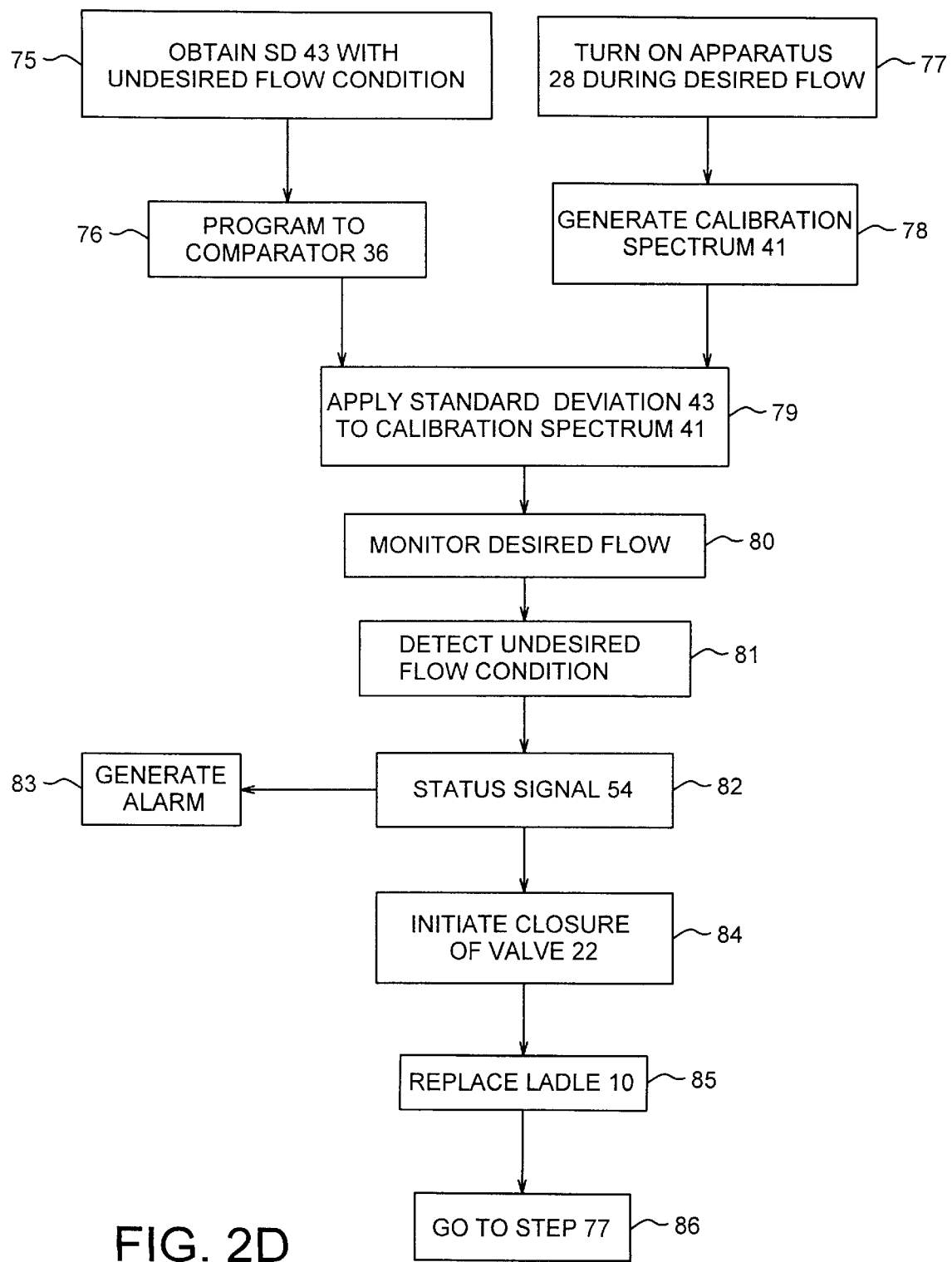

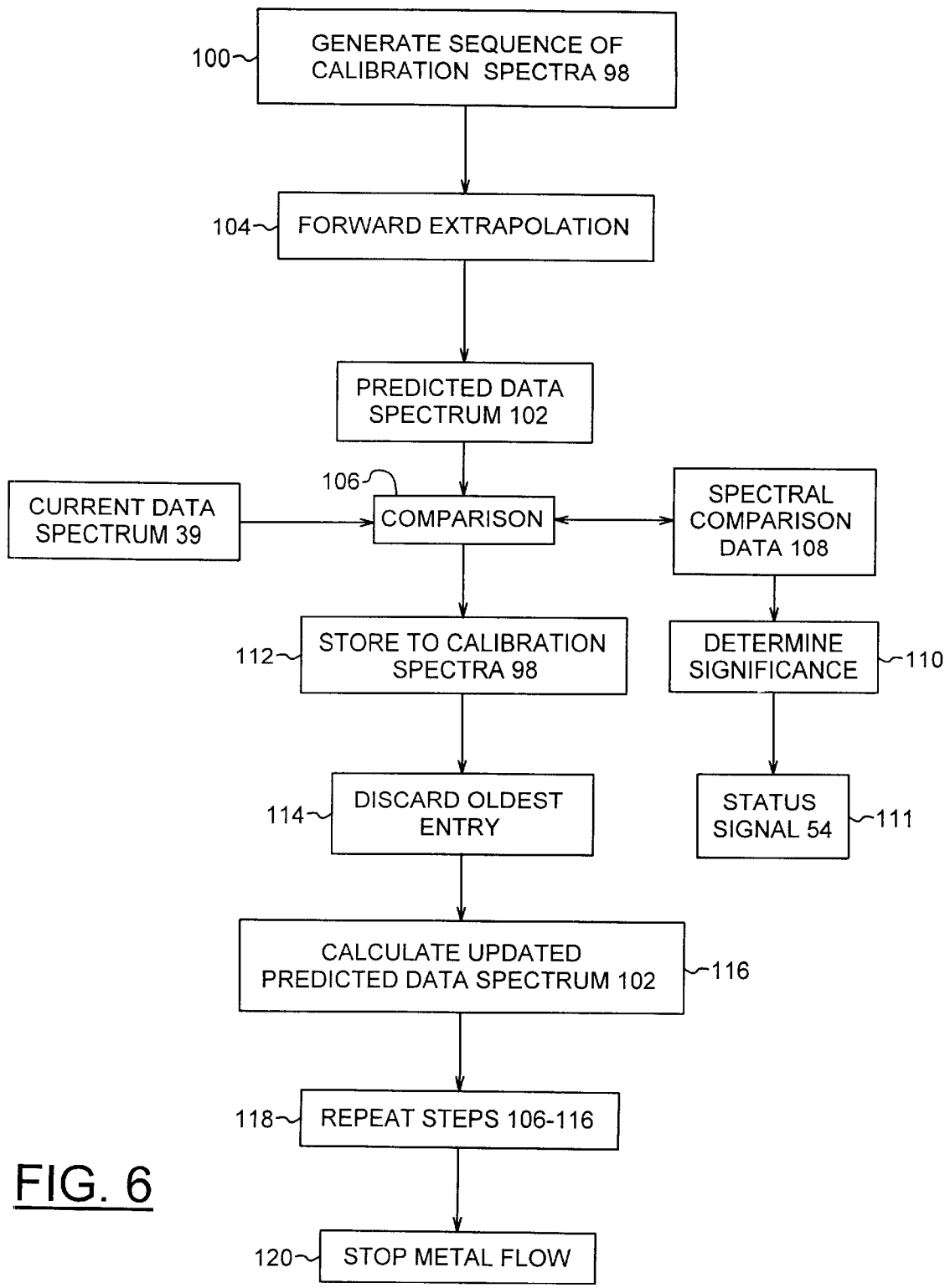

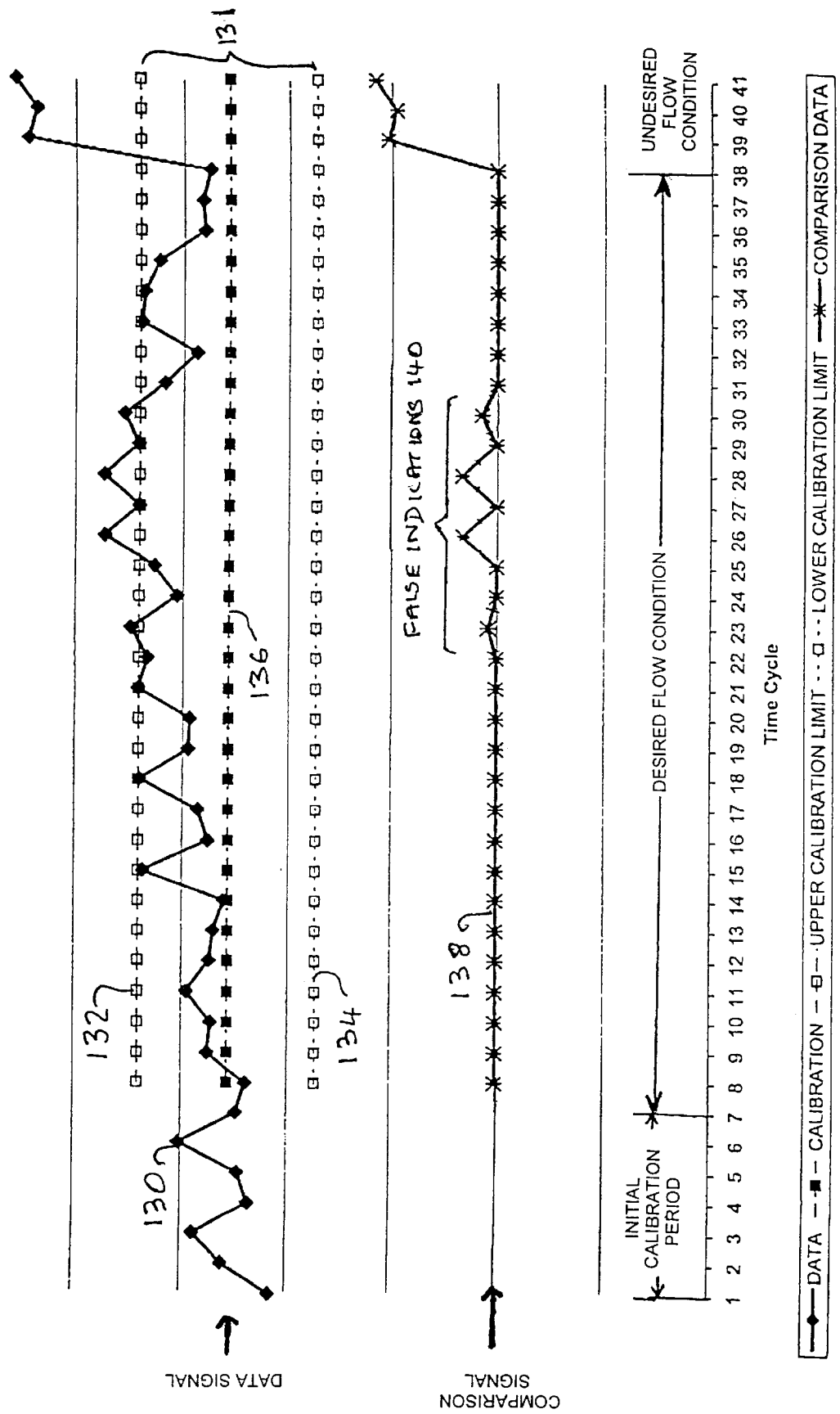

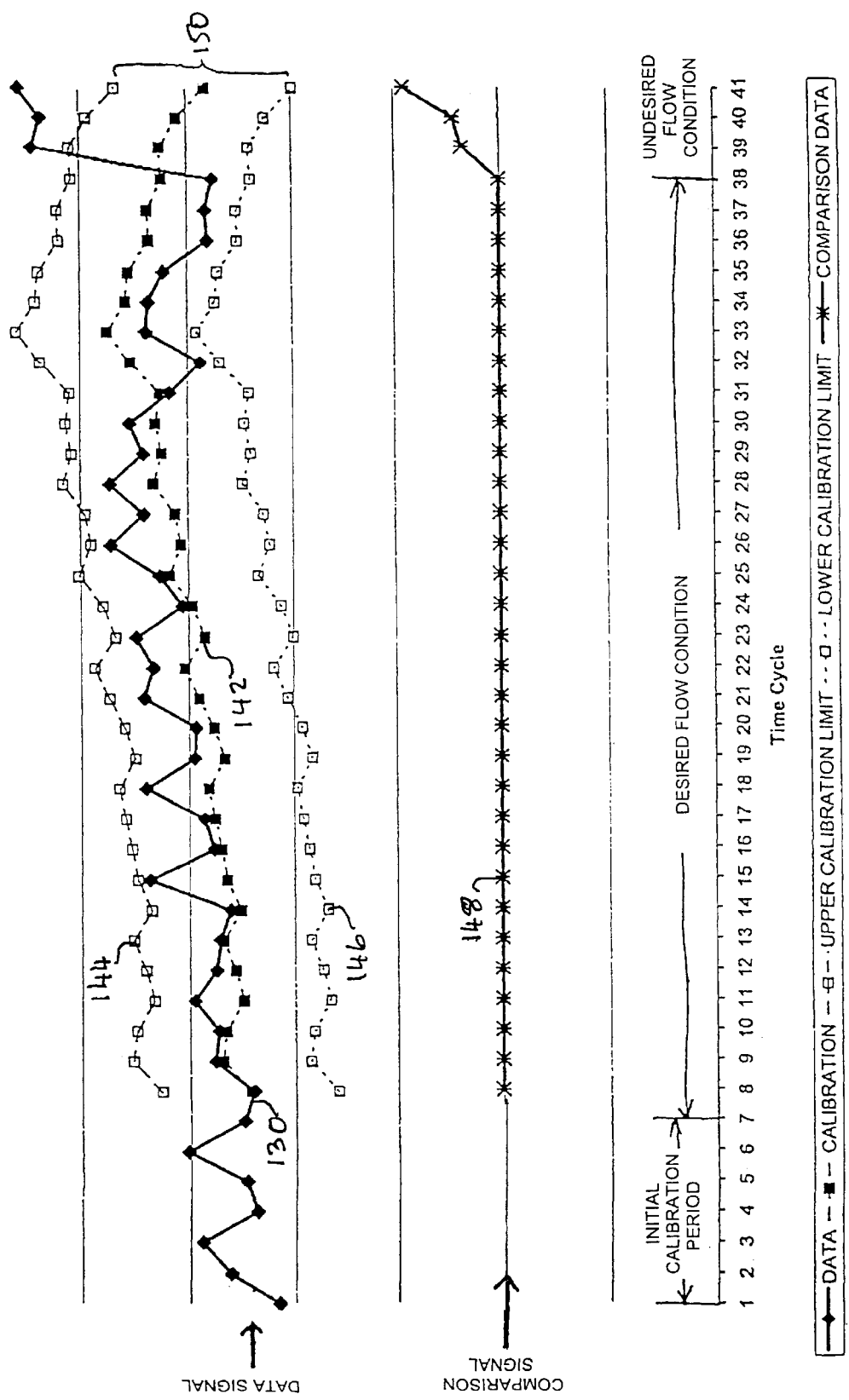

LIQUID METAL FLOW CONDITION DETECTION

This application is a continuation-in-part of application Ser. No. 09/097,401 filed Jun. 15, 1998 (abandoned), which is a continuation of application Ser. No. 08/745,067, filed Nov. 7, 1996 (abandoned) which in turn is a continuation of application Ser. No. 08/277,409 filed Jul. 19, 1994, now U.S. Pat. No. 5,633,462, dated May 27, 1997. The disclosure of U.S. Pat. No. 5,633,462 is hereby incorporated herein by reference thereto.

BACKGROUND OF THE INVENTION

1. Field of the Invention

The present invention relates to a method and apparatus for detecting the condition of the flow of liquid metal in or from a teeming vessel and more particularly to a method and apparatus for detecting the presence of an undesirable condition in the flow of liquid metal in or from the teeming vessel.

2. Description of Related Art Including Information Disclosed Under 37 CFR 1.97 and 37 CFR 1.98

Liquid metal and in particular liquid steel is drained from a draining or teeming vessel, normally a ladle, into one or more molds usually through an intermediate or receiving vessel, normally a tundish. In this process, a controlled flow of liquid metal passes from the ladle, normally through a nozzle and valve in the bottom of the ladle, into a ceramic tube and then into a receiving vessel, normally a tundish. A tundish is a refractory-lined vessel equipped with one or multiple outlets through which the metal flows into the mold(s).

As the teeming ladle approaches empty, slag and oxidation products which float on-top of the liquid steel in the ladle, can be entrained within the teeming flow and transferred to the tundish. Usually, as the teeming ladle is approaching empty, the surface of the liquid steel in the tundish is observed visually and when slag is seen to be entering the receiving vessel, the valve in the teeming ladle is closed in order to reduce the contamination of the metal in the tundish or mold with slag and oxidation products. Alternatively, an electromagnetic coil may be employed to assist in the detection of the presence of slag or non-metallics in the teeming flow and to automatically signal for valve closure. Typically, this coil surrounds the nozzle of the teeming ladle and senses variations of the electromagnetic field produced by the excitation of the coil related to changes in non-metallic content of the flow.

It is well known that flow from a teeming ladle induces vibration of the ladle itself, the ceramic tube which is attached to the ladle, and the tundish. In particular, vibration of the tube can be substantial. Attempts have been made to sense this vibration manually.

The prior art does not address the following problems:
Visual Slag Detection

Visibility of slag entrainment within the tundish is poor. Therefore, the ability of the ladle teeming operator to see slag is difficult and the consistency of ladle flow closure is poor. Early ladle closure results in lost metal yield and late ladle closure results in slag contamination of the liquid steel in the tundish. As multiple ladles are poured into one tundish, slag build-up occurs and the problem of visibility is compounded. A significant problem associated with visual slag detection is that slag is not seen until it is already present in the tundish.

Electromagnetic Slag Detection

The sensor coil is located in the ladle and therefore, is highly susceptible to thermal and physical damage. The ladle must be specifically adapted to accept the coil and as each ladle arrives at the teeming position, a cable connection must be performed. Steel penetration in the nozzle block can damage the coil or impede its operation. A teeming ladle must be removed from the operational cycle to replace a damaged or non-performing coil. In this situation, slag is not detected until it is present within the nozzle block of the teeming ladle and already flowing toward the tundish.

Prior Art Vibration Sensing

Manual vibration sensing is inconsistent and operator dependent. The human threshold to sense and discriminate change in vibration is limited. As with the above two methodologies, slag is detected when it is present and flowing through the tube attached to the ladle.

BRIEF SUMMARY OF THE INVENTION

Accordingly, it is an object of the present invention to provide a method and apparatus which utilizes vibra-acoustic signals to characterize and detect changes in the flow condition or behavior of liquid metal which presage the onset, or are characteristic of, slag entrainment within the metallic flow passing from a draining vessel.

Another object is to provide a logic which allows a means for flow discrimination and provides alarms which indicate a deviation between a desired flow condition of a ladle and undesired flow conditions such as vortexing, flow rate irregularity, surface collapse, flow plugging, slag entrainment, and gaseous aspiration.

It has been found that the above and other objects of the present invention are attained in an apparatus for detecting the condition of the flow of liquid metal in or from a teeming vessel including a sensor for detecting vibration caused by a flow of liquid metal in or from the teeming vessel and for outputting a sensor signal corresponding to an amount of vibration detected by the sensor. A signal processor receives the sensor signal and compares the sensor signal to a reference signal and outputs a comparison signal. A logic unit receives the comparison signal and outputs a status signal indicative of the condition of the flow of the liquid metal in or from the teeming vessel.

A method for detecting a condition of a liquid metal flow in or from a teeming vessel includes detecting an amount of vibration caused by the liquid metal flowing in or from the teeming vessel. The detected amount of vibration is converted to a sensor signal. The sensor signal is compared to a reference signal to output a comparison signal. A status signal is outputted in response to the comparison signal, the status signal being indicative of a condition of the flow of the liquid metal in or from the teeming vessel.

BRIEF DESCRIPTION OF THE SEVERAL VIEWS OF THE DRAWING

Some embodiments of the invention, and of making and using the invention, as well as the best mode contemplated of carrying out the invention, are described in detail below, by way of example, with reference to the accompanying drawings, in which like reference characters designate like elements throughout the several views, and in which:

FIG. 2D is a schematic flow diagram summarizing the flow detection process illustrated in FIGS. 2–2C;

FIG. 6 is a schematic block flow diagram illustrating in more detail the inventive embodiment of the invention illustrated in FIG. 5.

FIG. 7 is a graphic representation of results obtainable with a static calibration flow condition detection method, according to the invention, such as is described with reference to FIGS. 2–2D;

FIG. 8 is a graphic representation of results obtainable with a dynamic calibration flow condition detection method, according to the invention, such as is described with reference to FIGS. 5–6.

DETAILED DESCRIPTION OF THE INVENTION

The present invention relates to a method and apparatus which discriminates vibration associated with liquid metal flow, slag or slag-contaminated liquid metal flow, and alterations in flow behavior or condition which presage the onset of slag entrainment within the metallic flow passing from a teeming or draining vessel such as a ladle.

Figure 1:
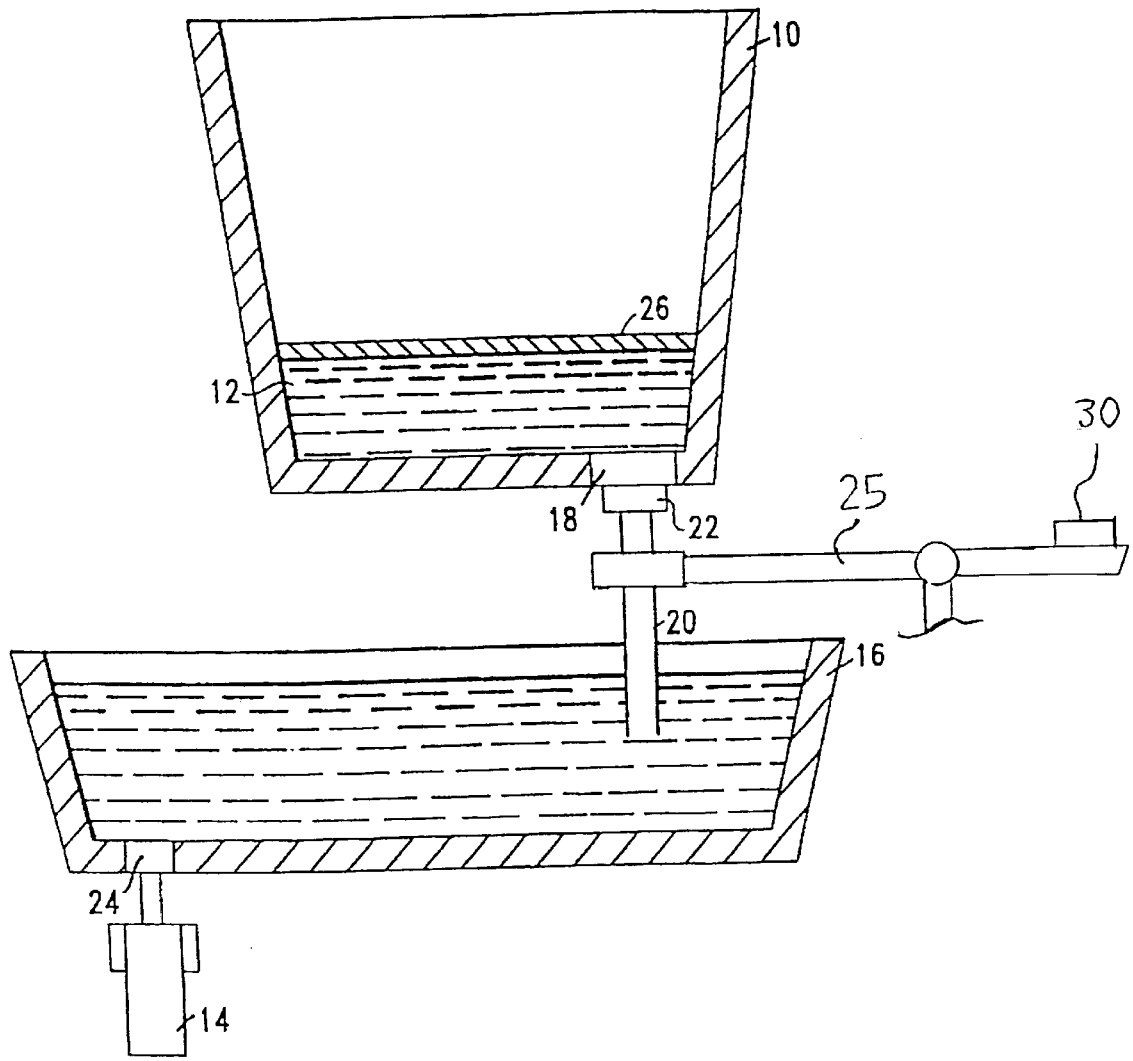
FIG. 1 is a typical arrangement in a steel making process showing apparatus used to pour liquid metal from a teeming vessel or ladle and ultimately into a mold.

Referring now to the drawings wherein like numerals indicate like elements, there is shown in FIG. 1 a general arrangement of prior art apparatus typically used in a continuous casting steel making process in which the presence of contaminants in the flow of liquid metal is sought to be detected. In the continuous casting process, a draining vessel or ladle 10 is filled with liquid metal 12 and transfers the liquid metal 12 into one or more molds 14 through an intermediate or receiving vessel called a tundish 16. A controlled flow of the liquid metal 12 passes from the ladle 10 to the tundish 16 through a nozzle 18 located in the bottom of the ladle 10, and through a ceramic pouring tube 20, which is preferably a ceramic tube. The nozzle 18 includes a valve 22 to control the rate of flow of the liquid metal 12 out of the ladle 10. The tundish 16 is equipped with one or more outlets 24 through which the liquid metal 12 flows into a corresponding (i.e. one or more) number of the molds 14. A holding arm 25 supports tube 20 for detachment from ladle 10 and attachment to a new ladle. A vibration sensor 30 is mounted on holding arm 25 remotely from tube 20, where it will be unaffected by heat from tube 20.

When the ladle 10 contains little or no liquid metal 12, the ladle 10 is replaced with another ladle, not shown, filled with liquid metal 12 to insure that the liquid metal 12 flows continuously to the mold(s) 14. When the second ladle, not shown, similarly runs out of the liquid metal 12, it too is replaced with another ladle, not shown, filled with liquid metal 12. This is a continuous process.

A problem with continuous steel casting arises when the ladle 10 approaches empty. The presence of an impurity such as slag 26, which typically forms a layer on the liquid metal 12, becomes entrained in the liquid metal 12 passing through the valve 22 and the tube 20. This contaminates the liquid metal 12 passing into the tundish 16, and ultimately into the mold(s) 14. This is undesirable.

When the ladle 10 is filled with the liquid metal 12, the presence of the slag 26 or other impurities floating on top of the liquid metal 12 is far enough away from the nozzle 18, that the slag 26 does not become entrained with the liquid metal 12 passing from the ladle 10 to the tundish 16. The flow of the liquid metal 12 from the tundish 10 and through the nozzle 18 at that point is, therefore, an uncontaminated flow, or a substantially uncontaminated flow.

The method and apparatus of the present invention uses vibration sensing, analysis, and alarm logic for the discrimination of the flow of the liquid metal 12 from the ladle 10. This process provides alarms which indicate a deviation between the desired condition of the flow of the liquid metal from the ladle 10, and undesired flow conditions such as slag entrainment as the ladle 10 approaches empty. It is within the scope of the present invention to detect other undesirable flow conditions such as vortexing, flow rate irregularity, surface collapse, flow plugging, and gaseous aspiration.

Alarms are provided to indicate undesirable changes in flow condition. Alarms associated with vortexing, and/or flow rate irregularity, and/or surface collapse can presage the onset of slag flow or entrainment. The present invention can be used to aid the human operator in deciding to stop the flow by closing the valve 22. Alternatively, alarm logic can provide a signal to automatically or manually initiate closure of the valve 22.

Figure 2:
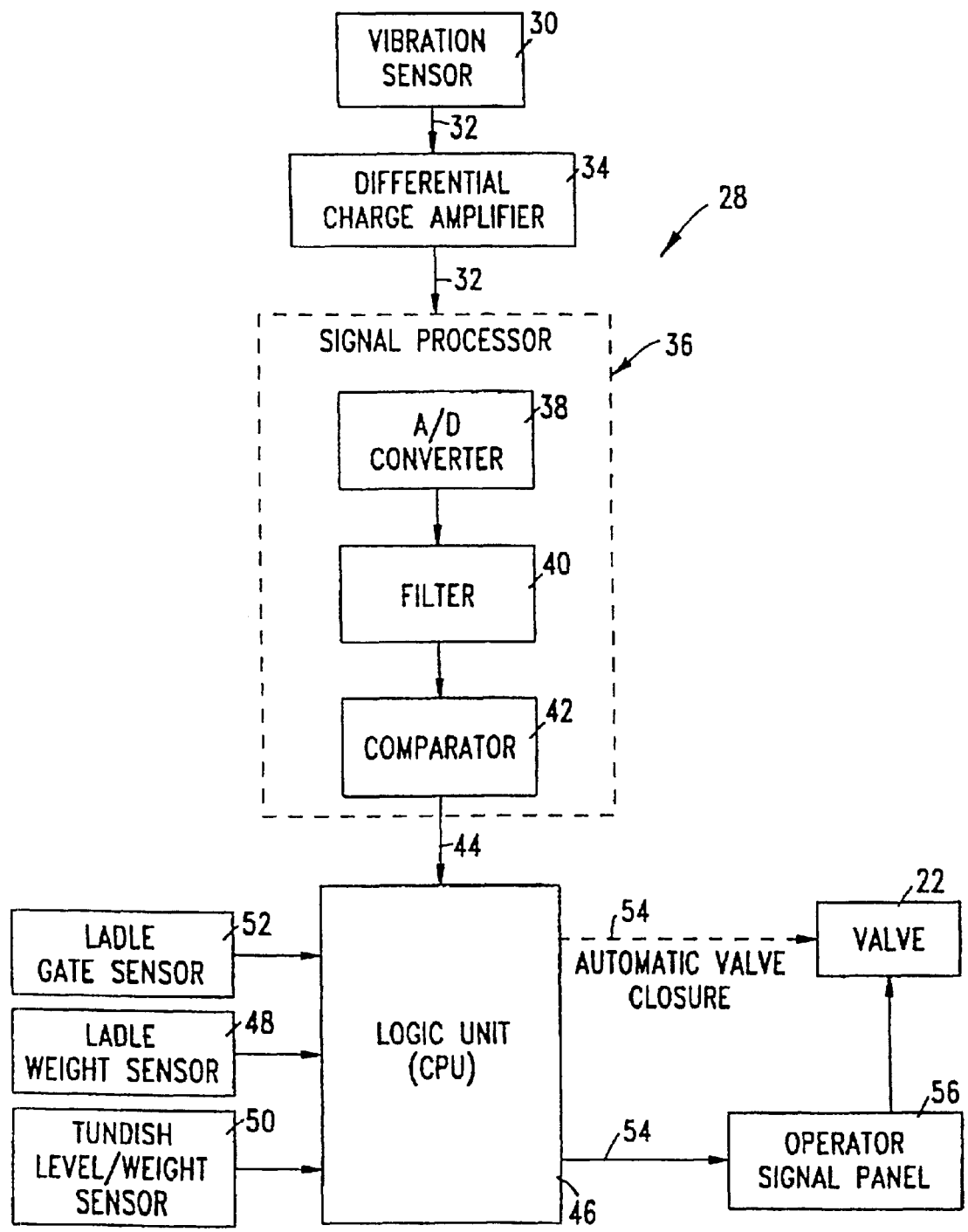
FIG. 2 is a schematic diagram showing the elements used to detect an undesirable flow condition in the flow of liquid metal in and from the teeming vessel or ladle of FIG. 1.
Figure 2A:
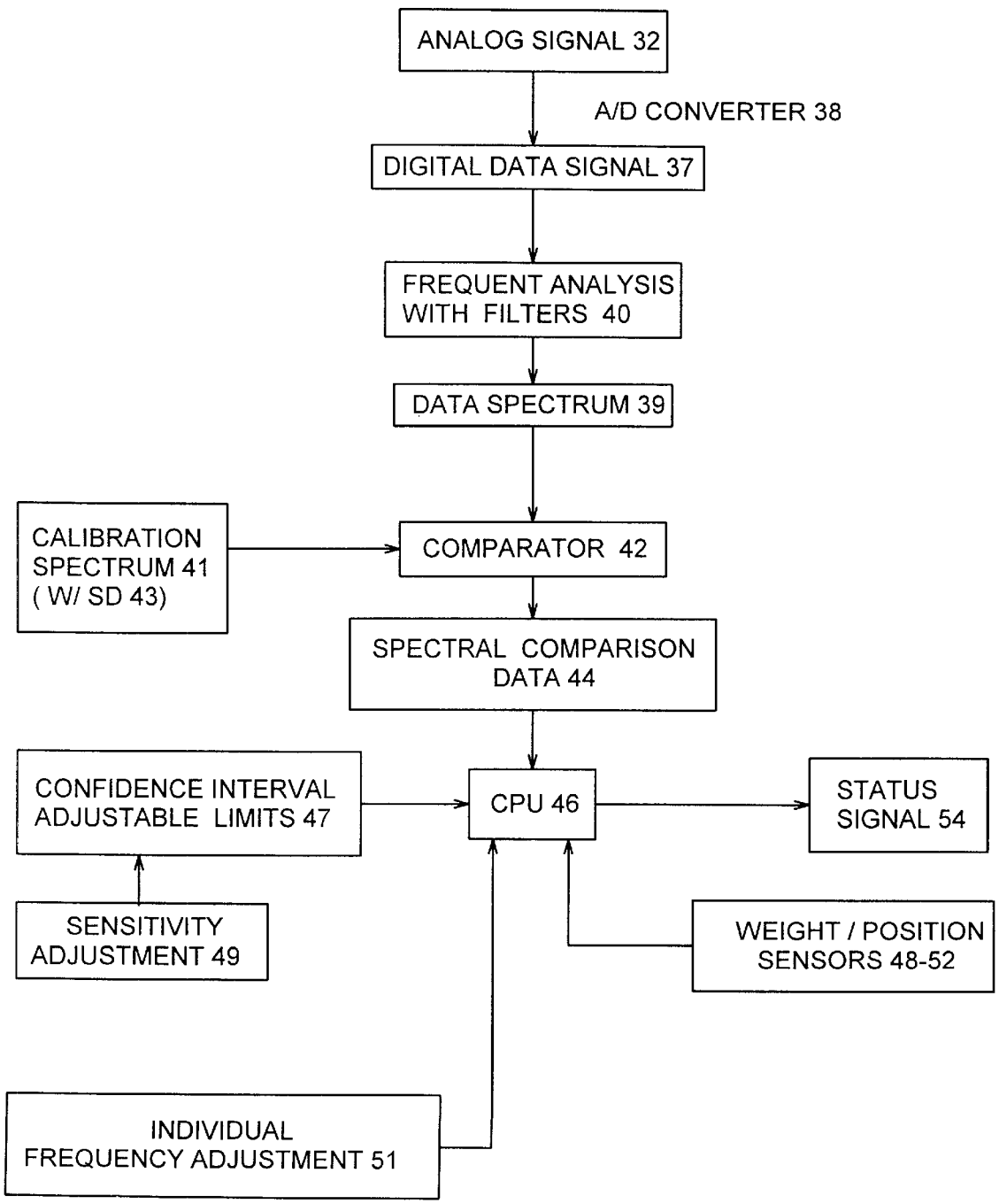
FIG. 2A is a schematic flow diagram illustrating one embodiment of a method of flow condition detection according to the invention and employing the apparatus elements shown in FIG. 2.

Referring now to FIGS. 2 and 2A, there is shown at 28 a general arrangement of the method and apparatus of the present invention for detecting the condition of the flow of the liquid metal 12 in and/or from the ladle 10. A vibration-sensing device or sensor 30 such as a microphone, or in a preferred embodiment a delta-shear type accelerometer, is used to sense the vibration induced by the flow of the liquid metal 12 in or from the ladle 10. The vibration sensor 30 outputs an analog electrical signal or sensor signal 32 which allows measurement of the vibration. The accelerometer can be obtained from any of the known suppliers including Bruel & Kjaer of Denmark or Hewlett Packard.

The sensor 30 may be coupled to the vibration source by any of the known methods, e.g. bolts or magnetic means. It is not required that the sensor 30 be in direct contact with the liquid metal flow channel. For example, the sensor 30 can be coupled directly to the ceramic tube 20 if the sensor 30 is able to withstand temperatures associated with the ceramic tube 20. In a preferred embodiment, the sensor 30 is coupled to a lifting device, not shown, which moves the tube 20 into and out of alignment with the ladle 10 and tundish 16. The sensor 30 can be coupled to the tube 20 or the lifting device, not shown, by a magnet. Alternatively, the sensor 30 can be bolted directly to the ceramic tube 20 or lifting device or any other elastic solid, i.e. a solid capable of passing vibration, which is in direct contact with the vibration source.

Once the vibration sensor 30 generates the sensor signal 32, it is passed to a differential charge amplifier 34 consisting of two high gain, low noise operational amplifiers. A filter network around the input amplifier provides a fall-off in response below 10 Hz. This eliminates the influence of low frequency noise from the sensor signal 32 which could be caused by the effects of fluctuating temperature. Preferably, the charge amplifier 34 has a balanced low-impedance output suitable for drawing, i.e. passing signals, through long cables. The charge amplifier can be obtained from any of the known suppliers, including the suppliers described above.

The sensor signal 32 from the charge amplifier 34 is passed to analysis electronics or an analysis unit 36 such as a signal processor for continuous analysis. The analysis or signal processing of the sensor signal 32 allows for the discrimination of the signal 32. In a preferred embodiment, the analysis/signal processing is performed by a real-time frequency analyzer which allows rapid frequency analysis and simultaneous spectral comparison such that no signal data is lost. The signal processor can be obtained from any of the known suppliers, including the suppliers described above.

Within the signal processor 36, the analog sensor signal 32 is first converted to a digital data signal by an analog-to-digital converter 38. In a preferred embodiment, the analog sensor signal 32 is converted to a digital data signal 37 internally by a signal analyzer using a nine-pole elliptical low pass filter which supplies at least 84 dB of attenuation of high-frequency signals.

During and/or after conversion, the digital data signal is processed using constant-percentage bandwidth filters 40 to divide the digital data signal into those portions associated with various frequency bands over the frequency range of interest, e.g. a frequency range of 0.1 Hz to 20 kHz. This is referred to as frequency analysis. The output of the frequency analysis is a data spectrum 39.

Data spectrum is rapidly and continuously generated and compared to a calibration spectrum 41 by a comparator 42. Calibration spectrum 41 is generated for the desired flow condition (i.e. free of vortices, slag, contaminants, etc.). In the comparator 42, data spectrum 39 is continually laid over calibration spectrum 41 to determine when the intensity level of data spectrum 39 is outside a preprogrammed standard deviation 43 which is an integral part of calibration spectrum 41. This is referred to as spectral comparison.

The differences between data spectrum 39 and calibration spectrum 41 are calculated by the comparator 42 and yield spectral comparison data 44. The magnitudes of the spectral comparison data 44 are processed within a logic unit or central processing unit ("CPU") 46. In a preferred embodiment, the CPU 46 is a Compaq 486DX266 IBM compatible programmable computer, although it should be realized that other types and brands of CPU's are within the scope of the present invention, e.g. Apple computers, RISC based computers, Silicon Graphics work stations or the like.

The CPU 46 generates a status signal 54 such as a contaminant or flow condition change warning signal and/or a ladle shut-off signal using a logic based upon the magnitudes of the spectral comparison data 44. This logic is based upon the magnitude of the variance of the spectral comparison data 44 outside of about 88% to 95% confidence intervals. In other words, the difference between the real time generated data spectrum and calibration spectrum 41 is calculated at frequent intervals (typically on the order of 500–1000 milliseconds) and the logic assumes that variance in this difference larger than a specific confidence interval placed around the calibration spectrum 41, is indicative of the alterations of flow condition which can be characterized at different spectral frequencies or bands such as vortexing, surface collapsing, flow rate, gaseous aspiration and/or slag entrainment.

The CPU 46 contains adjustable limits 47 of the confidence interval and the magnitude of the differences between the adjusted confidence interval and the measured spectral data, to allow the adjustment of the sensitivity of the system to the flow condition changes previously defined. In addition, the logic allows the independent adjustment 51 of the confidence interval associated with individual frequencies or bands in order to allow the adjustment of the sensitivity of the system to the different flow conditions which are experienced.

The logic can simply involve the presence of a specific magnitude of the spectral comparison data 44 or can include a time history, and/or ladle weight factors to enhance alarm sensitivity. The CPU 46 can have as input, signals from steel making process equipment such as the ladle weight determined from a ladle weight sensor 48, the tundish level or weight determined from a tundish level/weight sensor 50, and/or the ladle gate or valve position determined from a ladle gate or valve position sensor 52. This allows the sensitivity of the logic to be varied as a function of ladle weight, and for the system to automatically control and close the ladle gate or valve 22. For example, as the ladle 10 gets closer and closer to empty, the likelihood of slag entrainment or a similar undesirable flow condition is increased and the sensitivity of the logic is increased accordingly.

The output from the CPU 46 is used to pass the status signal 54 to the operator signal panel 56 which indicates the state, e.g. an alarm state, of the flow condition. The status signal 54 can be used to aid the operator of the signal panel 56 in deciding whether to stop the flow of liquid metal by closing the valve 22. The status signals 54 may also be used to signal for, or automatically initiate closure of, the ladle valve 22.

In use, the method and apparatus 28 of the present invention is first used to determine standard deviation 43 for calibration spectrum 41 for the flow of liquid metal in the particular steel making process for which the condition of the flow of the liquid metal is sought to be detected, such as the process shown and described in FIG. 1. Standard deviation 43 is then preprogrammed into the signal processor 36 and applied to calibration spectrum 41. This is subsequently compared with data spectrum 39. Data spectrum 39 is continuously generated and updated to measure the most up to date condition of the flow of liquid metal.

Figure 2B:
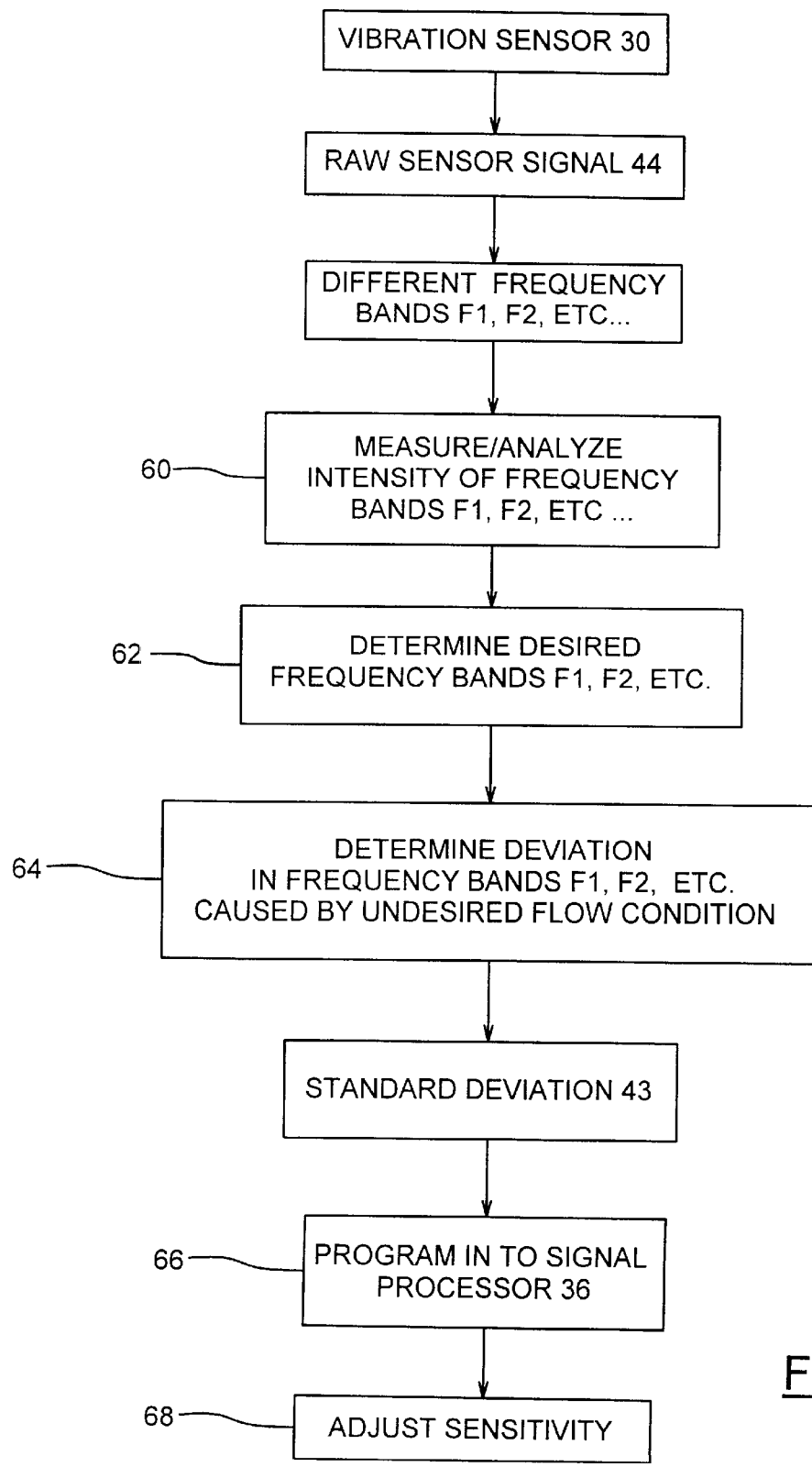
FIG. 2B is a schematic flow diagram illustrating the determination of a calibration standard deviation for use in the flow condition detection method shown in FIG. 2A.

Referring now to FIG. 2B, to determine the standard deviation 43 to be applied to the calibration spectrum 41, the flow of the liquid metal is analyzed. The vibration sensor 30 is attached to the steel making equipment used in the steel making process to generate the sensor signal 44 in the manner described above. The raw signal 44 is then broken up into different frequency bands F1, F2, etc., by the filter 40 of the signal processor 36 into a range between about 0.1 to 20 kHz. The intensity of each of these frequency bands is then measured and analyzed, step 60, to determine which frequency bands respond to the flow conditions that are sought to be detected, e.g. slag entrainment, step 62 For flow conditions or events such as slag entrainment that generate low end noise, the lower end of the frequency band, between about 10 Hz–1 kHz, need only be considered.

Figure 3:
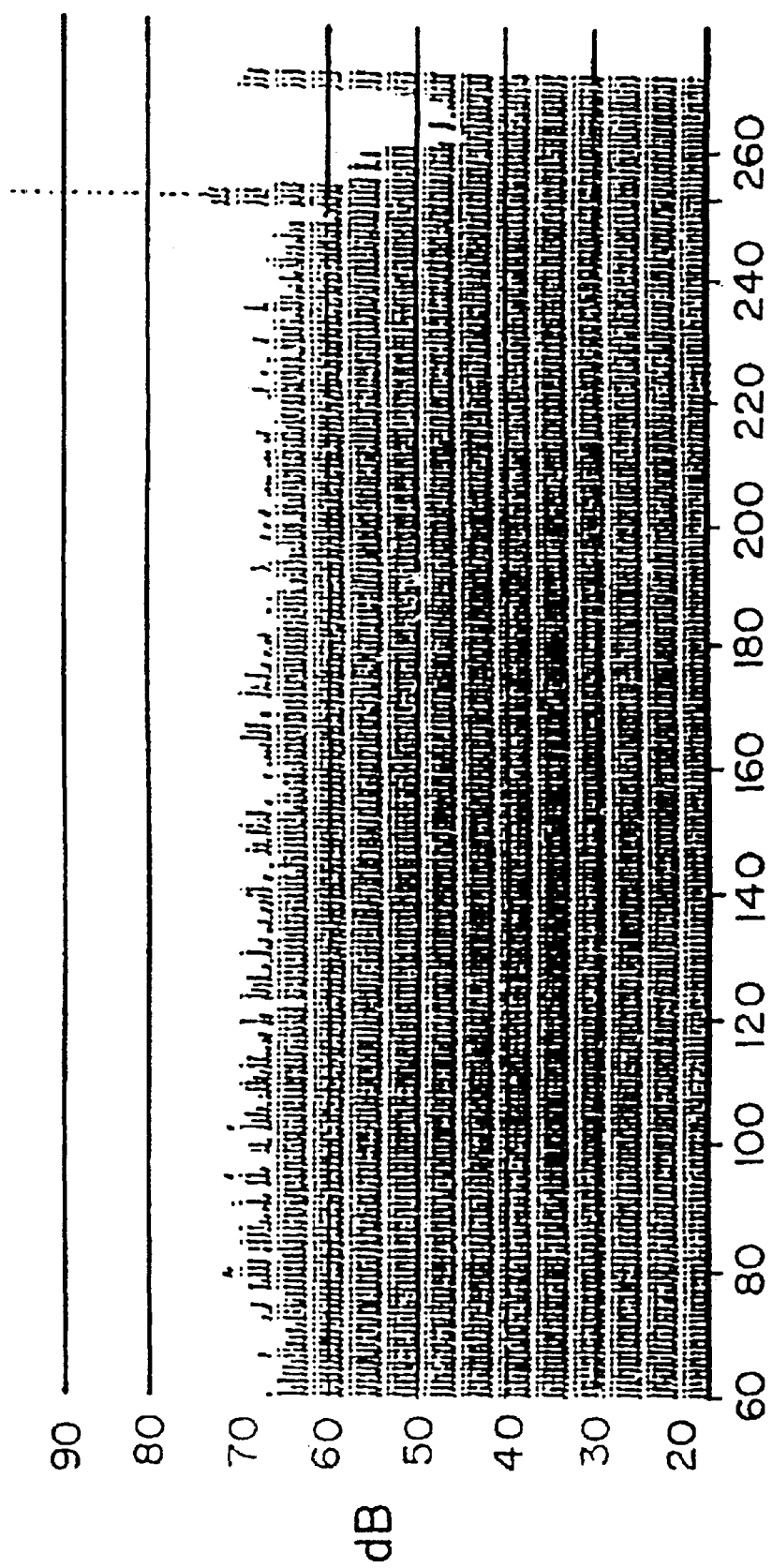
FIG. 3 is a graph representing a change in signal intensity at 40 Hz associated with an undesirable flow condition, such as slag entrainment or carryover.
Figure 4:
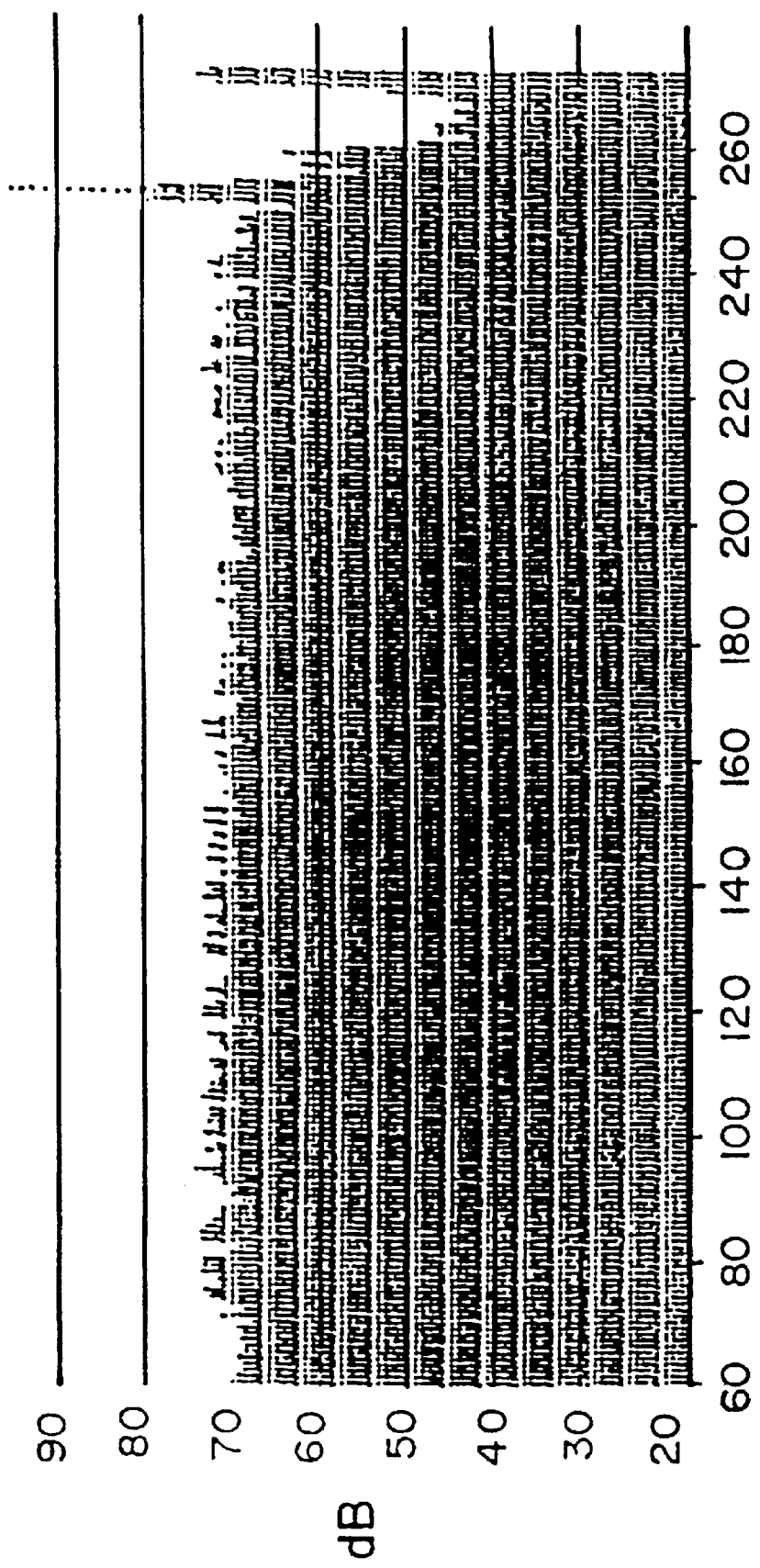
FIG. 4 is a graph representing a change in signal intensity at 50 Hz associated with an undesirable flow condition, such as slag entrainment or carryover.

Referring now to FIGS. 3, 4, two representative frequency bands are shown therein that have been generated for determining an exemplary standard deviation which may be applied to a calibration spectrum. FIG. 3 illustrates a 40 Hz signal, F1, and FIG. 4 illustrates a 50 Hz signal, F2. The unit of the y-axis is dB and the unit of the x-axis is time. FIGS. 3, 4 were are generated during a typical run of the method and apparatus of the present invention 28 in connection with a given steel making process such as the one shown and described at FIG. 1.

For the particular steel making process from which FIGS. 3, 4 were generated, the strong drop noted at the end of the graphs is associated with slag 26 passing through the ceramic tube 20 between the ladle 10 and the tundish 16. The intensity of the signal levels for both figures are fairly constant until the change in the flow of the liquid metal 12 associated with slag entrainment. The small spikes in FIGS. 3, 4 just before the large drop can be associated with vortexing within the tube 20 just before slag entrainment or carryover.

From FIGS. 3, 4 the frequency bands F1, F2 are determined to deviate in intensity approximately +5, −15 dB, step 64. In other words, in FIGS. 3, 4 the intensity level of an uncontaminated flow of liquid metal at 40 and 50 Hz, respectively, is approximately 70 dB. Once the flow of liquid metal is contaminated with slag or when some other undesirable flow condition occurs, the intensity of the frequency bands generated by the flow of the liquid metal deviates +5, −15 dB. It should be realized by those skilled in the art that while the analysis of only two frequency bands, F1, F2, as set forth in FIGS. 3, 4 is described herein, all of the frequency bands within the range of 0.1 Hz–20 kHz should be analyzed, although the lower end of the frequency band, approximately between 10 Hz–1 kHz, need only be analyzed in a steel making process which typically generates low frequency noise, i.e., less than 1 kHz.

Once the standard deviation 43 to be applied to the calibration spectrum 41 is determined, it is programmed into the signal processor 36, step 66. Standard deviation 43 can be increased or decreased to decrease or increase, respectively, the sensitivity of the method and apparatus 28, step 68. The apparatus 28 of the present invention is now ready to detect the condition of the flow of liquid metal in the desired steel making process, such as the one shown and described in FIG. 1

Figure 2C:
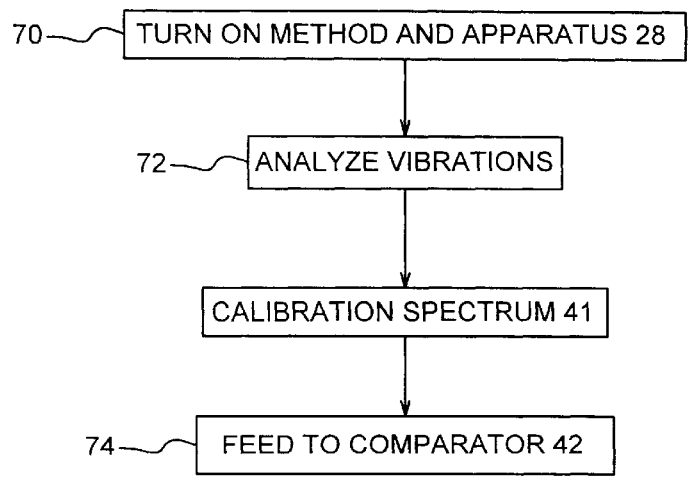
FIG. 2C is a schematic flow diagram illustrating the generation of a calibration spectrum for use in the flow condition detection method shown in FIG. 2A.

Referring now to FIG. 2C, in a preferred embodiment, the method and apparatus 28 of the present invention is turned on, step 70 when the amount of liquid steel 12 in the ladle 10 approaches approximately 20 tons to first generate calibration spectrum 41 to which standard deviation 43 is applied. A typical ladle used in a steel making process holds anywhere between 100–300 tons of liquid metal. At 15–20 tons of liquid metal 12 remaining in the ladle 10, the flow of the liquid metal 12 out of the ladle 10 is a substantially uncontaminated flow, although it should be realized by those skilled in the art that the apparatus 28 of the present invention can be turned on at any level of the liquid metal 12 in which the flow of liquid metal is not contaminated or in an undesirable condition to generate the calibration spectrum 41.

To generate calibration spectrum 41, the vibration of the flow of the liquid metal 12 passing through the ceramic tube 20 is analyzed by the signal processor 36, step 72, in the manner described above for approximately three to fifteen seconds. This information is then fed into the comparator 42, step 74.

After calibration spectrum 41 is generated and fed into the comparator 42, the vibration of the flow of the liquid metal 12 passing through the ceramic tube 20 is analyzed by the signal processor 36 in the manner described above to generate he data spectrum 39. The comparator 42 of the signal processor 36 then compares the intensity of the frequency of vibration of the flow of liquid metal 12 traveling through the ceramic tube 20, i.e. the data spectrum 39, with standard deviation 43 applied to the calibration spectrum 41 to generate the spectral comparison data 44 which is fed into the CPU 46. Data spectrum 39 is constantly updated and compared with standard deviation 43 applied to the calibration spectrum 41 to reflect the latest flow conditions.

The CPU 46 analyzes the spectral comparison data 44 to determine if the data spectrum 39 is within standard deviation 43 applied to calibration spectrum 41. If the spectral comparison data 44 determines that data spectrum 39 deviates outside standard deviation 43 applied to calibration spectrum, the CPU 46 is programmed to determine the extent of the deviation, e.g. how much data spectrum 39 deviates from the calibration spectrum 41, and for how long. If the deviation is determined by the CPU 46 to be acceptable, a positive status signal is passed to the operator signal panel 56. If the deviation is determined by the CPU 46 to be unacceptable, the status signal 54 declares an alarm state. This information is passed to the operator signal panel 56 to inform the operator of the signal panel 56 of the alarm state so that he can initiate closure of the valve 22, if appropriate. Alternatively, the status signal 54 in the alarm state can initiate automatic valve closure of the valve 22.

Once the valve 22 is closed, the ladle 10 is replaced with another ladle filled with liquid metal, not shown. When the amount of liquid metal contained in the second ladle approaches 15–20 tons, the method and apparatus 28 is again turned on and operated in the manner described above. A new calibration spectrum is generated and applied to the preprogrammed standard deviation and compared to a data spectrum in the manner described above. This is a continuous process.

Referring to the process summary of the flow detection method of the invention illustrated in FIG. 2D, a suitable standard deviation 43 is obtained in a preliminary step 75, and programmed to comparator 42, step 76, by sensing vibrations during a typical liquid metal pouring run and during an undesired flow event, as described with reference to FIGS. 2B and FIGS. 3–4.

To detect slag outflow, or another undesired condition, during pouring of liquid steel from a given ladle 10, apparatus 28 is turned on during substantially uncontaminated flow from the ladle, step 77, and a calibration spectrum 41 specific to the particular ladle 10, is generated, step 78. Standard deviation 43 is applied to calibration spectrum 41, step 79, and the desired flow in ladle 10 is monitored, step 80, by continuously comparing signals received from sensor 30 with calibration spectrum 41, into which standard deviation 43 is integrated.

When the sensor signal sufficiently exceeds calibration spectrum 41, according to the preprogrammed standard deviation and any sensitivity adjustments, an undesired flow condition is detected, step 81, generating an event status signal 54, step 82. Status signal 54 can be used to generate an alarm, step 83, or to initiate closure of valve 22, step 84. Ladle 10 is then replaced with a new ladle 10, step 85, the pouring process is repeated and the flow detection process of the invention commences again by going to step 77, step 86.

Figure 5:
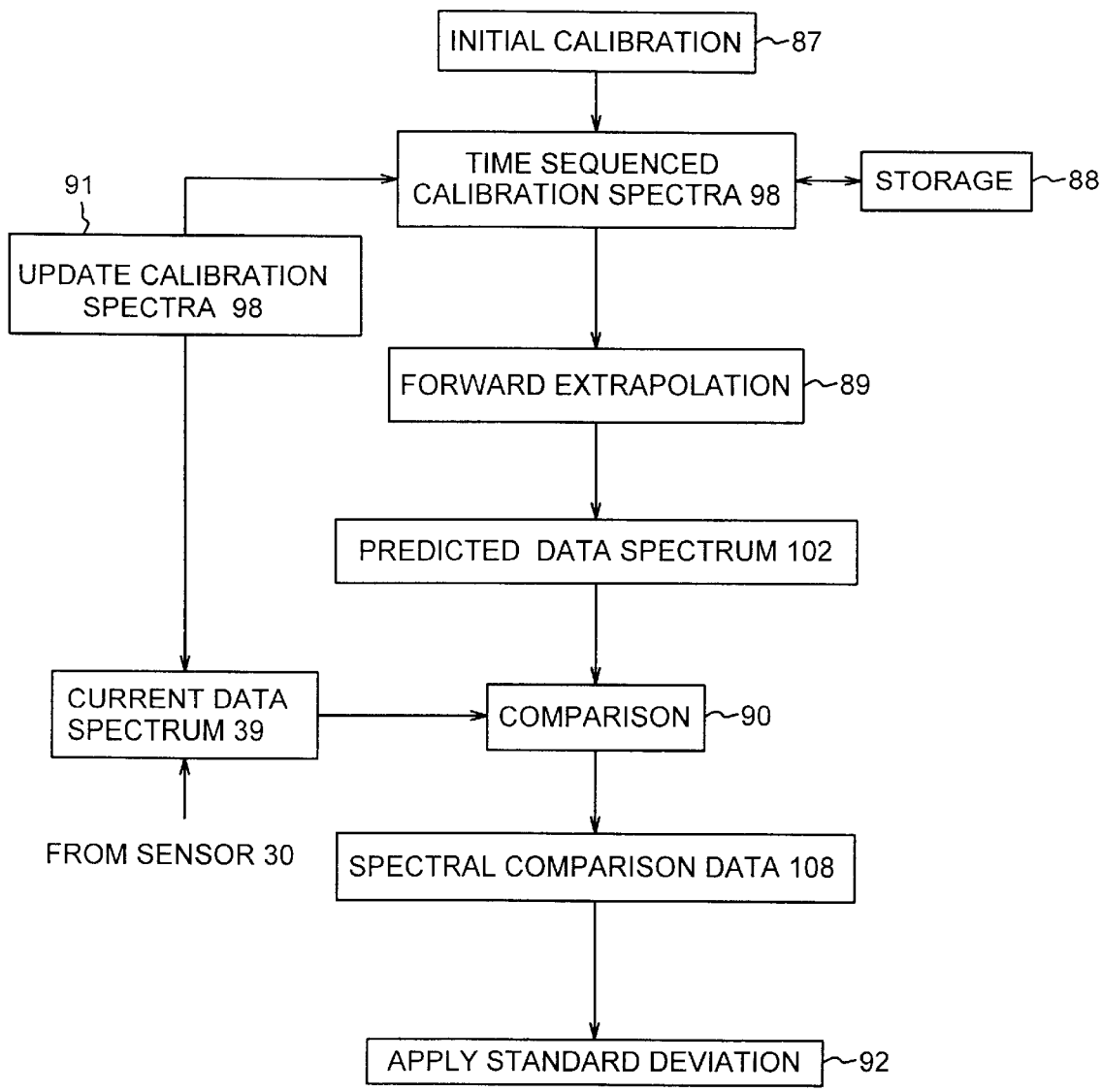
FIG. 5 is a schematic block flow diagram illustrating in overview another embodiment of flow condition detection system according to the invention, employing dynamically updated calibration spectra to detect fast-acting changes in the flow.

Referring now to FIG. 5, the alternative embodiment of the invention shown can achieve a high level of functionality, with good yields of slag-free, or low slag metal product, by dynamically updating the calibration spectra employed for flow condition detection so as to be responsive to fast-acting changes indicative of imminent slag entrainment or outflow. In this embodiment, the calibration spectrum becomes a predicted data spectrum that can be updated on each cycle of the logic unit, as will now be described. In this way, it becomes possible to detect time-related changes in the frequency or amplitude, or in both attributes. In effect the differential of the desired attribute can be monitored and used to initiate a system response, enabling fast-changing phenomena to be detected and acted upon, if appropriate.

The illustrated flow condition detection method can be performed by a flow condition detection system such as that referenced 28 in FIG. 2, installed, for example, in a continuous casting steel process of the type shown in FIG. 1. As shown, vibration sensor 30 is mechanically coupled to pouring tube 20 to sense vibrations in the molten steel flowing through pouring tube 20 from ladle 10, which for the purposes of illustration will be assumed to have a 300 ton capacity, although it could of course have any desired capacity. Flow condition detection system 28 is coupled with valve 22 for valve 22 to be operated automatically in response to a negative status signal 54. When the net ladle weight drops to about 20 tons, as indicated by ladle weight sensor 48, flow condition detection system 28 is turned on, initiating a calibration routine. Turning flow condition detection system 28 on earlier risks premature activation of valve 28 caused by random external noise picked up by sensor 30, for example hammering.

The method as illustrated in overview in FIG. 5 comprises an initial calibration step 87 in which time sequenced calibration spectra 98 are generated by monitoring desirable flow conditions with sensor 30 and sent to storage, step 88. Calibration spectra 98 are statistically analyzed and a predicted data spectrum 102 for flow conditions at a point in future time is generated by forward extrapolation of the data, step 89.

A current data spectrum 39 is then obtained, for example from sensor 30, and is compared with predicted data spectrum 102, in comparison step 90 to generate spectral comparison data 108. Current data spectrum 39 is also employed to update calibration spectra 98, step 91, by adding the data spectrum to the calibration spectra 98 as the latest entry in the time sequence, and discarding the oldest entry. If desired, a suitable standard deviation or other function can be applied to predicted data spectrum 102 to facilitate interpretation of the spectral comparison data. Spectral comparison data 108 are processed by the logic unit to provide a status signal such as status signal 54, if the spectral comparison data 108 are found to be significant, indicating an undesired flow condition such as imminent slag entrainment or outflow, or another recognizable undesired condition, such as described herein. Status signal 54 can initiate a warning and be acted upon, if appropriate.

Preferably, update step 91 is effected on each cycle of the logic unit, or less frequently in synchronism with the logic unit cycle. Preferably also, the cycle of steps 90, 91, 89 and 102 is repeated until the flow of metal is stopped.

The method illustrated in FIG. 5 can be performed, in the logic unit, for example in CPU 46, without requiring the comparator function 42 in signal processor 36 (FIG. 2), enabling a high level of signal-processing functionality as computer capabilities rapidly evolve.

In this manner, the time history capabilities of the logic unit are useful for dynamically updating the calibration spectra. Preferably, calibration spectra 98 are repetitively updated after each comparison with a current data spectrum providing a calibration process that is not static but dynamic, is self-correcting and has a time history that can be used to predict the current data spectrum.

As described, an object of the invention is to detect changes in the flow conditions and to indicate significant deviation from desired flow conditions. Pursuant to this embodiment of the invention it has been discovered that certain changes in the flow condition which are undesirable and therefore need to be detected are relatively fast-acting. Furthermore, slow-acting changes that occur may not be indicative of a significant deviation from a desired flow condition.

By dynamically self-correcting adjustment of the calibration spectrum in the logic unit, as described herein, slow-acting changes occurring between the calibration spectra 98 and the obtaining of a current data spectrum 39 will be ignored as these changes become dynamically included within the updated sequence of calibration spectra 98.

The spectral comparison data 108 are accordingly particularly sensitive to fastacting changes that have been found, pursuant to the invention, to be especially indicative of significant deviation between desired and undesired flow conditions.

Referring now to FIG. 6, and considering the method described in FIG. 5 in more detail, the method commences with an initial calibration period during which a time-dependent sequence of calibration spectra 98 of sensed vibrations, is generated and stored, with retention of the sequential relationship, step 100. Unlike the embodiment illustrated in FIGS. 2–2C which employs what may be regarded as static calibration spectra, in the present embodiment, the sequence of calibration spectra 98 are dynamically updated, as described and explained in more detail hereinbelow. Various ways of generating suitable calibration spectra 98 will be apparent to those skilled in the art from the teachings herein. In a preferred embodiment, the initial calibration period is from about 3 to about 15 seconds in duration. Calibration preferably commences under desirable, essentially slag-free pouring conditions where no slag is present in ceramic tube 20. Sufficient readings are taken to provide a meaningful reference database. However, calibration should not be so prolonged as to average out, or miss, a meaningful trend in the data. From about 10 to about 50 readings will usually be a suitable number.

In one example, twenty calibration readings, numbered 1–20, are taken with a processing cycle time of about 250 milliseconds ("ms" hereinafter) enabling about four readings per second to be taken, with an elapsed time of about 5 seconds for the calibration period. The resulting sequence of calibration spectra 98 is stored in RAM, accessible to CPU 46, as a time-dependent history record, and are optionally also sent to permanent storage. As noted above, CPU 46 can be a programmable personal computer, identified by its processor "486DX2 66", which can embody significant RAM (random access memory) storage as well as hard disk data storage capabilities, suitable for the practice of this embodiment of the invention. CPU 46 preferably carries out the data processing and storage functions required by the inventive slag detection method and can include suitable software to manage and effect these functions. The time history capabilities inherent in such a computer system are employed to create and maintain dynamically updated calibration spectra 98.

Each calibration reading preferably comprises a spectrum of vibration amplitude variation with frequency, as sensed by sensor 30, in a user-selected frequency range, implemented by system logic. A flow condition detection management program provides operator selection of a desired frequency range, for example, in the present preferred embodiment a range of from about 40 Hz to 1.2 kHz, a low frequency audible, or barely audible range. Remote uploading of these and other-operator selected parameters, and downloading of data, can also be provided, by suitable wired or wireless communications devices, for example a dial-up modem, which may be connected with CPU 46, if desired.

A predicted data spectrum 102 can then be calculated by forward extrapolation of the sequence of stored calibration spectra 98, step 104. Forward extrapolation step 104 can be effected by statistically analyzing the changes over time in calibration spectra 98 and predicting one or more readings that are to be expected to be obtained at a specific point or points in future time, according to an appropriate data change model.

A preferred specific point in future time for which predicted data spectrum 102 is calculated can be when a future data spectrum will become available, for example, on the next process cycle or a point on the next process cycle which is one complete cycle ahead of the last calibration reading. Any desired technique can be used for forward extrapolation. With a relatively small number of data points, straight line extrapolation can be employed. However, if statistical analysis of the data points indicates some other time-related trend in the data points, such as a geometric or exponential progression, or other more complex progression, a corresponding more sophisticated extrapolation technique can be employed, as will be understood by those skilled in the art of statistical modeling.

Predicted data spectrum 102 is preferably calculated as a continuous spectrum but can be calculated as a desired number of data points, at frequencies of interest, distributed in the frequency spectrum of interest, if desired.

In data comparison step 106, a current data spectrum 39 is obtained from signal processor 36, by CPU 46, or other suitable logic unit, for example comparator 42, and compared to predicted data spectrum 102, to determine and generate spectral comparison data 108. indicating differences between the sensed current data spectrum and the predicted data spectrum. These differences, if present may be indicative of changes in the physical flow phenomena of the molten metal and may presage slag outflow. However random, or other, interfering vibrations may also be detected.

Spectral comparison data 108 are processed by the CPU 46 to determine their significance, step 110, and a status signal 54 is generated, step 111. Each selected frequency band F1, F2, etc. is discretely processed, included in, and compared with, calibration spectra 98 to generate its own comparison signal component of spectral comparison data 108. If desired, significance determination step 110 can weight a particular selected frequency band or bands, to give responses from that frequency band or bands, more or less significance in the decision process.

Preferably, user-variable and determinable confidence limits are provided to CPU for evaluation of the significance of the comparison data. If the comparison data meet user-determined criteria indicating a significant change, predictive of slag outflow, then status signal 54 has warning or alert characteristics. If the comparison data are evaluated as not showing a significant change, status signal 54 has a character indicating normal flow characteristics.

At the same time as, or immediately subsequently to, spectrum comparison step 106 and significance determination step 110, current data spectrum 39 is also used to update calibration spectra 98, by adding current data spectrum 39 to calibration spectra 98, as the most recent entry in the sequence, step 112, and discarding the oldest entry in the sequence, step 114. An updated predicted data spectrum 102, is then calculated, step 116, by forward extrapolation of the stored calibration spectra 98, as described above. In this way, the calibration spectra are dynamically updated to provide the most current available data background against which to evaluate a current reading for emerging changes.

The steps from comparison step 106 to step 116 where updated predicted data spectrum 102 is calculated, including steps 108, 110, 112 and 114, are repeated cyclically, step 118, until spectral comparison data 108 is determined to be significant in step 110. A negative status signal 54 is then generated, indicating the presence, or preferably, the imminent presence, of slag at valve 22 or ceramic tube 20. In response to the negative status signal, the flow of metal is stopped, step 120, and, preferably, a warning is issued, which is preferably both audible and visible and can, if desired be communicated to a local or remote operator's computer screen or closed circuit television screen possibly using audio overlay and a character generator. Step 120, stopping the flow of metal, can be effected by closing valve 22, or by such other means as may be known.

Alternatively, or in addition, and depending upon the nature and significance of spectral comparison data 108, step 120 may not effect a complete closing of valve 22. Rather, valve 22 may be automatically operated to be partially closed and slow the flow of liquid metal. If a normal condition status signal 54 is then obtained, valve 22 can be re-opened whereas if status signal 54 deteriorates, then complete closure of valve 22 is effected. This process can permit over-reaction to false alarms while still assuring an effective response to a real slag outflow event.

Whereas the flow detection method described with reference to FIGS. 1–4 generates spectral comparison data having the form of the magnitudes of differences, the dynamic updating method illustrated in FIGS. 5–6 enables spectral comparison data providing information regarding the slope or the rate of change of the spectral data to be generated. The dynamically updated sequence of calibration spectra 98 allows the calculation of this rate of change and its employment in the status signal logic.

The spectral comparison data, which are indicative of changing vibration characteristics at the examined frequencies, can, optionally, be compared with a dynamically updated standard deviation envelope to determine the significance of the data. If the comparison data is not significant, monitoring continues. If the comparison data is significant, an undesired flow condition status signal alarm is issued.

The standard deviation envelope places significance limits on the comparison data which may be determined empirically or by experiment with typical pouring vessels and conditions as described hereinabove. Preferably the characteristics of the standard deviation envelope, are varied according to the detected conditions. Alternatively, the standard deviation envelope may simply apply a selected proportionate increase to the magnitude of each data point in the spectral comparison data.

Preferably, the dynamic calibration method illustrated in FIGS. 5–6 also includes analysis of the signal into one or more frequency bands F1, F2, etc. which are individually processed for changes which occur within that frequency band, as described in connection with FIGS. 2–2D. The system may then respond to a significant change within a given frequency band, to any significant change within any of the bands or to a composite change within multiple bands. The number of bands may vary widely. For example only one band might be selected if a particular frequency band provides responses of interest. However multiple bands, up to perhaps 1,000 may be desirable, if the equipment is capable of processing the requisite number of data signals. Preferably, from about 5 to about 100 frequency bands F1, F2, etc. are generated, more preferably from about 10 to about 40 bands. In one preferred embodiment about 20–22 bands are generated, and from about 4 to about 20 bands are selected for monitoring in a frequency spectrum of interest, for example for monitoring the flow of molten steel, from about 10 Hz to about 1 kHz. Alternatively, if desired, the signal may be processed as a substantially complete spectrum within a relatively wide acoustic frequency range, and the system may then respond to one or more significant changes detectable in a predetermined time interval.

Referring now to FIG. 7 a data signal 130 from one frequency band, e.g. 50 Hz, of a current data spectrum 39 is shown superimposed upon a static calibration window 131 defined between equally spaced upper and lower calibration limits 132, 134 on either side of a calibration signal 136. Calibration signal 136 can be obtained from calibration spectrum 41 generated as described with reference to FIG. 2C. Calibration limits 132–134 may correspond with, or be derived from, standard deviation 43 which is preferably determined as described with reference to FIG. 2B, and is selected to provide a desired confidence level, e.g. 90%. The frequency band of data signal 130 is selected for responsiveness to an undesired flow condition, for example slag outflow, or imminent slag outflow.

A complete data spectrum 39 preferably comprises multiple frequency bands F1, F2, etc. each, or some, of which may be selected to provide a data signal such as data signal 130. Each frequency band can be analyzed using the method described hereinabove with reference to FIGS. 2–2D and may have features comparable with those shown for data signal 130, albeit with particular characteristics that may vary significantly as between one frequency band and another.

Shown below data signal 130, is a comparison signal 138 calculated by comparison of data signal 130 with the calibration window 131. Beneath comparison signal 138 may be seen a time cycle scale divided into an initial calibration period, from cycles 1–7, a desired flow condition period from cycles 7–38 and an undesired flow condition period from cycle 38 on, as labeled. A key to the graphic symbols appears along the bottom of FIG. 7.

During the initial calibration period, only data signal 130 is active. At the end of the calibration period, calibration window 131 is calculated from the data signal obtained during the initial calibration period. As shown, calibration signal 136 is approximately an arithmetic average of the magnitudes of the data signal readings in time cycles 1–7, but other calculations may be employed.

Calibration window 131 is a static base against which the constantly changing data signal 130 is compared. As long as data signal 130 lies within calibration window 131, as defined by its limits 1–134, comparison signal 138 is constant. However when data signal 130 moves outside calibration window 131, calibration signal 136 changes in relation to the magnitude of the deviation between upper calibration limit 132 and data signal 130.

In the example illustrated by FIG. 7, a desired flow condition exists until cycle 38 after which time an undesired flow condition suddenly occurs causing data signal 130 to move significantly above upper calibration limit 132 at cycle 39 and beyond.

However, static calibration window 131 fails to track the relatively slow upward trend in data signal 130 in the period from cycles 1–30 so that false indications 140 of an undesired flow condition are given by fluctuations in comparison signal 138 at various times prior to cycle 38, as indicated at cycles 23, 26, 28 and 30. To avoid premature cessation of pouring, caused by false indications 140, various steps can be taken. For example, limits 132–134 can be increased, causing sensitivity to be reduced. Alternatively, an operator, logic unit, can await confirmation of indications such as false indications 140 before stopping the flow of liquid metal. While either tactic may be acceptable, it would be preferable to avoid such false indications without sacrificing sensitivity or responsiveness. Dynamic calibration, as described with reference to FIGS. 5–6, and as illustrated in FIG. 8, can solve this problem.

The graphs shown in FIG. 8 illustrate an identical data signal 130 to that shown in FIG. 7, and as in FIG. 7, only data signal 130 is active during the initial calibration period. Once this initial period is complete, data signal 130, obtained during the calibration period is used to predict, by forward linear extrapolation, as described with reference to FIGS. 5–6, a forward value for current data signal 130, and this prediction becomes the calibration level, referenced 142. Upper and lower calibration limits 144, 146 are placed around the calibration level and comparison signal 148 is obtained from the comparison of data signal 130 with calibration limits 144, 146 in the same way as in the static calibration example of FIG. 7.

Calibration level 142 is continually updated as data signal 130 is updated pursuant to the novel dynamic calibration method of the invention, as described hereinabove, and as may be seen from FIG. 8, tracks the slow upward trend of data signal 130. This novel dynamic characteristic is effective in eliminating false indications 140 of undesired flow condition found in the method employed in FIG. 7, because the data points for data signal 130 now lie within the calibration window 150 between calibration limits 144, 146. However, when the undesired flow condition occurs as illustrated after cycle 38, it is still detected by changes in the magnitude of comparison signal 138. At this point it can be seen that data signal 130 is now diverging sharply away from its previous trend, as is clearly indicated by the downward direction of calibration window 150.

It will be understood by those skilled in the art that various parameters of the calibration and signal comparison processes can be substantially varied, within the spirit of the invention, and that different liquid metal flows, different teeming vessels, pouring tubes and other differences that occur in different practical environments, can benefit from an appropriate selection of these parameters which may differ significantly from the preferred examples described herein. Some parameters that may be varied are the number of calibration readings taken, the duration of the calibration period, the cycle period and the magnitude of the standard deviation applied.

The number of calibration spectra readings taken and added to the calibration sequence should be sufficient to provide a statistically meaningful normalization of the variations between readings, but not so large as to mask significant trends or introduce an undesirable lag in the calibration level 142. From about 3 to about 100 calibration spectra are suitable, with from about 5 to about 25 being preferred. The duration of the calibration period will generally be the time required to take the desired number of readings and can vary from about 1 second to 1 minute, preferably from about 3 to about 15 seconds, as stated hereinabove. The lower limit will usually be determined by equipment capabilities, while the upper limit should not be so long as to interfere with proper detection of an undesired flow condition.

The cycle period is preferably about 250 to about 500 milliseconds, but may vary between about 10 milliseconds and about 2 seconds. Shorter cycle times are generally desirable, to enhance responsiveness, and the limit will usually be determined by the processing equipment's ability to complete the required signal processing steps on each cycle.

It is also contemplated that the number of calibration spectra 98 in the sequence may be varied during the course of a pouring from a teeming vessel to be, if desired. As may be seen from FIG. 8, calibration level 142 can approximate a smoothing of data signal 130, with a time lag, the degree of the smoothing and the duration of the time lag being determined by the number of calibration spectra 98 that are maintained in the calibration sequence. For example, while a given number of calibration spectra 98 may be satisfactory initially, if data signal 130 becomes unduly volatile during the pouring, without signaling an undesired flow condition, it may be desirable to increase the number of calibration spectra, for example by selective removal of old spectra, perhaps by removing a calibration spectrum from the sequence on every other cycle rather than every cycle, or by another suitable method. Alternatively, if the data signal is more stable, the number of calibration spectra may be reduced, for example by removing the two oldest spectra on a limited number of cycles, to provide greater sensitivity to fastacting changes.

It will be understood that the above-described simple "FIFO" first-in, first-out method of cycling calibration spectra 98 is only one of a number of possible algorithms that can be employed to update them. Other suitable algorithms and patterns for dynamically updating the calibration data will be apparent to those skilled in the art. For example, it may be desirable to effect the update two or three or more readings at a time, to smooth out relatively rapid interfering or otherwise insignificant perturbations. Thus, at every third new reading, the latest three spectra would be added to the calibration spectra sequence 98 and the three oldest readings would be removed or rejected. After the first and second new readings, the calibration spectra would be left unchanged. Other suitable statistical techniques for updating the calibration spectra sequence 98 to fulfil the purposes of this invention will be apparent to those skilled in the art.

Dynamically updating the calibration spectra, pursuant to the invention provides a powerful way of processing sensed vibration data in near real time to yield meaningful information regarding significant, fast-acting changes in the metal flow condition.

In another embodiment of the inventive method, where analysis of historical data indicates that certain identifiable, but erratic vibration patterns having amplitude or frequency spikes occur repetitively, for example repetitive banging or hammering, such vibration patterns can be filtered out by comparison with a prior such pattern. Such filtering can be effected in a step of pre-screening spectral comparison data 108 immediately prior to significance determination in step 110. Where the spectral comparison data 108 fit a prior erratic vibration pattern to a desired degree of significance, they can be rejected as insignificant, generating a normal or exception, but non-alerting status signal 54. The repetition interval must be sufficiently long that significant trends are not inadvertently filtered out or treated as insignificant.

Figure 9:
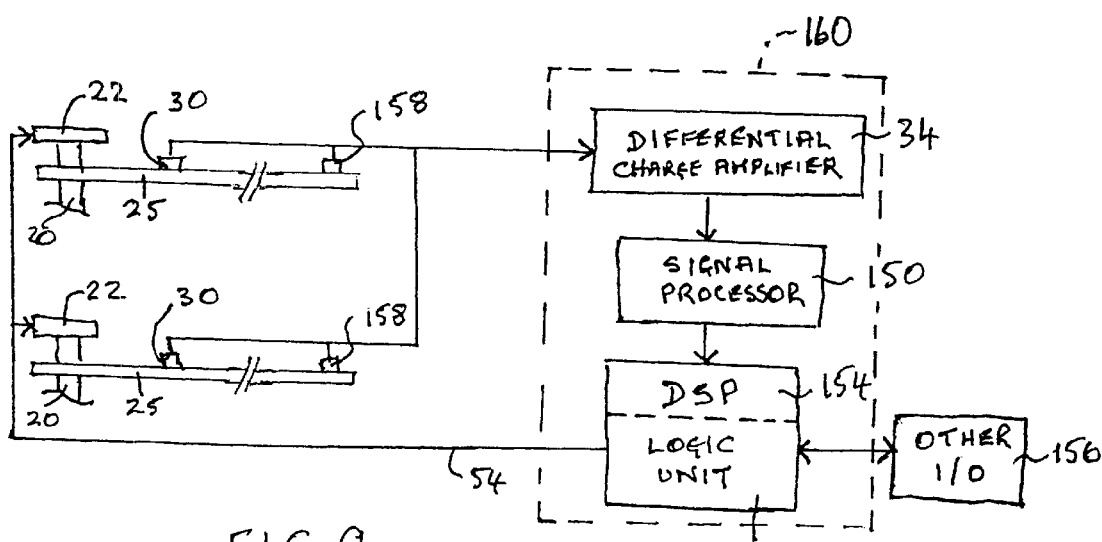
FIG. 9 is a schematic diagram similar to FIG. 2 showing the elements of a flow detection apparatus according to another embodiment of the invention.

Referring now to FIG. 9, the flow detection apparatus shown is a modified embodiment of the apparatus shown in FIG. 2 and comprises multiple vibration signal sensors 30, of which two are shown, attached to the respective holding arms 25 for the outflow tubes 20 of multiple tundishes or other teeming vessels (not shown). The outputs of sensors 30 are supplied separately to differential charge amplifier 34 and to a signal processor 150 comprising A/D conversion and frequency analysis functions but lacking the signal comparison functions performed by comparator 42 in the FIG. 2 embodiment. The digitized multiple frequency signals output from signal processor 150 are supplied to a logic unit 152 which comprises a digital signal processor module ("DSP")154 which effects comparison of the data signal 130 with the calibration signal. An undesired condition status signal 54, when generated by logic unit 152, is supplied to a respective one of valves 22 to stop the respective metal flow. The valve shut-off signals can either be physically isolated, employing separate conductors or can be electronically addressed to the proper valve 22.

Logic unit 152 also comprises other inputs/outputs as described with reference to FIG. 2, and otherwise as is conventional. Logic unit 152 is preferably a state-of-the-art personal computer, for example, in early 2001, a DELL OPTIPLEX (trademark, Dell Computer Corporation) GX200 system with an 866 MHz PENTIUM III (trademark, Intel Corp.) processor, 256 MB RDRAM and a 20 GB hard drive.

One suitable digital signal processor, which can be installed in logic unit 152 as a plug-in card, is a model PCI445x supplied by National Instruments. DSP 154 co-operates with, and is controlled by, logic unit 152. DSP 154 and logic unit 152 can jointly effect desired signal processing, comparison and storage functions as required by the method illustrated in FIGS. 2–2D, employing static calibration, as well as generation and maintenance of a sequence of calibration spectra 98 for dynamically updated calibration, and comparison of data signal 130 with same, for a selected number of frequency bands F1, F2, etc., as required by the method illustrated in FIGS. 5–6. Communication between DSP 154 and logic unit 152 can be effected over the logic unit's high speed system bus; which is a distinct advantage over external communication with comparator 42, in the FIG. 2 embodiment.

Optionally, in addition to a signal sensor 30, each holding arm 25 bears, attached in the same manner as signal sensor 30, in direct solid-to-solid physical contact therewith, a noise sensor 158. Noise sensor 158 is preferably an identical device to vibration sensor 30, e.g. a delta-shear accelerometer, but is physically spaced apart from signal sensor 30 in a manner enabling it to sense noise reaching sensor 30 but where event-related liquid metal vibrations are either not received or are greatly attenuated, for example at an end of holding arm 25 remote from pouring tube 20. Other suitable locations for noise sensors 158 will be apparent to, or can be determined, without undue experimentation, by those skilled in the art.

The data signal from signal sensor 30 can be modified by the noise signal from noise sensor 158, by any suitable method to enhance sensitivity, for example by subtracting the noise signal from the sensor signal.

As illustrated, a single flow condition detection apparatus 160 and associated sensors 30, and optionally also 158, can manage multiple metal streams via suitable couplings to their respective holding arms 25, or other suitable components and shut-off valves 22, if automatic, system-effected shut off is employed. Depending upon the processing capacity of flow condition detection apparatus 160, two, three, four, or possibly, in the future even more metal streams can be managed and monitored with simultaneous processing.

As described hereinabove, the preferred parameter that is sensed comprises what might be termed "natural" mechanical vibrations, including acoustic signals, that are induced in the liquid metal flow by perturbations in the liquid as it moves through the apparatus, much as water emanates distinctive gurgling sounds as it empties from a bathroom fixture. Preferably also, as described, the mechanical vibrations are sensed, or detected, by a vibration sensor 30, for example a piezoelectric accelerometer physically connected through solid components, such as holding arm 25 and ceramic tube 20. However, it will be understood that the inventive method of detecting and responding to variation of the vibrational signals which, in preferred embodiments comprises dynamically updating a reference or calibration signal, may also be beneficially employed when other parameters are sensed or when mechanical vibrations are detected across air separations. Examples of such other parameters are artificially induced mechanical vibrations and natural or artificially induced electrical or magnetic signals, at various frequencies.

Although the present invention has been described in relation to particular embodiments thereof, many other variations and modifications and other uses will become apparent to those skilled in the art. It is preferred, therefore, that the present invention be limited not by the specific disclosure herein, but only by the appended claims.

What is claimed is:

1. A method of detecting the condition of the flow of a liquid metal through an outlet from a teeming vessel, to indicate an undesired flow condition, the method comprising:
   a) generating a vibration calibration signal indicative of a desired flow condition of the liquid metal;
   b) sensing vibrations in the liquid metal flow;
   c) generating a sensor signal embodying information regarding the sensed vibrations;
   d) analyzing the sensor signal into a frequency band spectrum comprising multiple frequency bands;
   e) comparing at least one of the frequency bands with the calibration signal; and
   f) generating a status signal indicating an undesired flow condition in response to unacceptable differences between the sensor signal and the calibration signal.

2. A method according to claim 1 comprising outputting the frequency band spectrum for comparison with the calibration signal as a digital data spectrum.

3. A method according to claim 2 wherein the frequency band spectrum lies in a frequency range of from 0.1 Hz to 20 kHz.

4. A method according to claim 1 performed in a steelmaking process, the liquid metal being liquid steel, wherein the frequency band spectrum lies in a frequency range of from 10 Hz to 1 kHz.

5. A method according to claim 1 wherein the at least one frequency band compared with the calibration signal is selected from among the frequency bands available from analysis of the sensor signal as being a frequency band responsive to the undesired flow condition.

6. A method according to claim 1 wherein the sensor signal is an analog signal, the method further comprising converting the sensor signal to a digital data signal prior to comparing at least one of the frequency bands with the calibration signal, employing constant-percentage bandwidth filters to analyze the sensor signal into the frequency band spectrum and outputting the analyzed signal for comparison with the calibration signal as a digital data spectrum of frequencies.

7. A method according to claim 1 wherein the sensor signal is continuously analyzed into the frequency band spectrum by a real-time frequency analyzer permitting rapid frequency analysis of the sensor signal and wherein spectral comparison with the calibration signal is effected simultaneously with frequency analysis to avoid loss of signal data.

8. A method according to claim 1 wherein the liquid metal is steel, the frequency band spectrum is output as a rapidly and continuously generated digital data spectrum, the desired flow condition is a substantially slag-free flow condition and wherein the method further comprises:
   g) calculating a standard deviation for the calibration signal corresponding to acceptable differences between the sensor signal and the calibration signal;
   h) employing the calculated standard deviation when comparing the digital data spectrum to the calibration spectrum by continually laying the data spectrum over the calibration spectrum to determine when the intensity level of the data spectrum is outside the calculated standard deviation;
   and
   i) generating the status signal indicating an undesired flow condition when the differences between the data spectrum and the calculated standard deviation are unacceptable.

9. A method according to claim 8 comprising determining the magnitudes of differences in intensity between selected frequency bands of the data spectrum and the calibration spectrum, the frequency bands being selected for ability to indicate undesirable flow conditions, to yield spectral comparison data for generation of the status signal.

10. A method according to claim 1 wherein the calibration signal comprises a data spectrum of frequency intensities and a standard deviation is applied to the calibration signal for comparison with each frequency band whereby frequency band intensities exceeding the standard deviation of the calibration spectrum indicate an undesired flow condition.

11. A method according to claim 10 wherein the standard deviation is determined by sensing vibrations while pouring liquid metal from a teeming vessel, during an undesired flow event, in a preliminary step prior to flow detection.

12. A method according to claim 1 wherein the calibration signal is vessel-specific and is generated for each teeming vessel by sensing vibrations during desirable flow conditions through the teeming vessel, the method comprising using the vessel-specific calibration signal for comparison with the at least one frequency band to generate the status signal.

13. A method according to claim 12 comprising flowing liquid metal from a charged teeming vessel until a status signal indicating an undesired flow condition is generated and generating the vessel-specific calibration signal by sensing vibrations in the flowing liquid prior to occurrence of an undesired flow condition.

14. A method according to claim 13 implemented to monitor a flow of molten steel in a continuous casting process wherein molten steel is poured from successive teeming vessels through an outlet in each teeming vessel and wherein the method is repeated for each successive teeming vessel.

15. A method according to claim 13 comprising applying a standard deviation to the calibration spectrum used for comparison with the at least one frequency band, the standard deviation being determined by sensing vibrations in a liquid metal flow having undesired flow conditions.

16. A method according to claim 15 comprising effecting a sensitivity adjustment by increasing or decreasing the standard deviation.

17. A method according to claim 1 comprising generating spectral comparison data from the comparison of the at least one frequency band with the calibration signal and employing a logic unit to effect generation of the status signal by calculating the differences between the sensed signals and the calibration spectrum and generating the status signal indicating an undesired flow condition when the magnitude of the variance of the spectral comparison data is outside a predetermined confidence interval.

18. A method according to claim 17 comprising employing the logic unit to adjust the confidence interval and the magnitude of the differences between the adjusted confidence interval and the measured spectral data, to allow the adjustment of the sensitivity of the system to the flow condition changes previously defined.

19. A method according to claim 18 wherein individual said frequency bands have independently adjustable confidence intervals, the method comprising independently adjusting the confidence intervals to adjust the sensitivity of the system to different flow conditions.

20. A method according to claim 17 wherein the logic unit receives inputs from a teeming vessel weight sensor and a valve position actuator controlling outflow of liquid metal through the teeming vessel outlet to allow the sensitivity of the detection method to be varied as a function of teeming vessel weight and to enable automatic control and closing of the valve in response to an undesired flow condition.

21. A method according to claim 17 wherein the logic unit generates the status signal comprising employing the status signal to indicate an alarm state of the flow condition or to facilitate operator response or to automatically initiate closure of a valve controlling the liquid metal flow.

22. A method according to claim 1 comprising using an accelerometer to sense the vibrations in the liquid flow, the accelerometer communicating with the outlet through an elastic solid to receive vibrations from the liquid metal flow, the accelerometer being in direct contact with the elastic solid.

23. A method of detecting an undesired flow condition in a flow of molten steel in a continuous casting process wherein molten steel is poured from successive teeming vessels through an outlet in each teeming vessel, the method comprising:
a) commencing pouring of liquid steel from one of the successive teeming vessels through the teeming vessel outlet;
b) generating a vessel-specific vibration calibration signal indicative of a desired flow condition of the liquid metal during the pouring of the liquid steel from the one teeming vessel;
c) sensing vibrations in the liquid steel flow;
d) generating a sensor signal embodying information regarding the sensed vibrations;
e) comparing the sensor signal with the calibration signal;
f) generating a status signal indicating an undesired flow condition in response to differences between the sensor signal and the calibration signal;
g) replacing the one teeming vessel with a new teeming vessel charged with liquid steel; and
h) repeating elements b) through f) with the new teeming vessel.

24. A method according to claim 23 further comprising
i) analyzing the sensor signal into a frequency band spectrum comprising multiple frequency bands; and
j) selecting from among the multiple frequency bands a frequency band or bands responsive to the undesired flow condition and employing the selected frequency band or bands for comparison of the sensor signal with the calibration signal.

25. A method according to claim 23 wherein the calibration signal comprises a data spectrum of frequency intensities and a standard deviation is applied to the calibration signal for comparison with each frequency band whereby frequency band intensities exceeding the standard deviation of the calibration spectrum indicate an undesired flow condition.

26. A method according to claim 25 wherein the standard deviation is determined by sensing vibrations while pouring liquid metal from a teeming vessel, during an undesired flow event, in a preliminary step prior to flow detection.

27. A method of detecting the condition of the flow of a liquid metal, optionally molten steel, through an outlet from a teeming vessel, to indicate an undesired flow condition, the method comprising:
a) generating a vibration calibration signal indicative of a desired flow condition of the liquid metal;
b) applying a standard deviation to the calibration signal whereby vibration intensities exceeding the standard deviation of the calibration signal indicate an undesired flow condition;
c) sensing vibrations in the liquid metal flow;
d) generating a sensor signal embodying information regarding the sensed vibrations;
e) generating a status signal indicating an undesired flow condition in response to unacceptable differences between the sensor signal and the calibration signal.

28. A method according to claim 27 comprising determining the standard deviation by sensing vibrations while pouring liquid metal from a teeming vessel, during an undesired flow event, in a preliminary step prior to flow detection.

29. A method according to claim 28 wherein the calibration signal comprises a data spectrum of frequency intensities and the standard deviation is applied to the calibration signal for comparison with each frequency band whereby frequency band intensities exceeding the standard deviation of the calibration spectrum indicate an undesired flow condition.

30. A method of predicting an undesired condition in a liquid metal flow through an outlet from a molten metal pouring vessel, the method comprising the following elements:
a) sensing flow-related perturbations in a physical parameter indicative of the undesired condition of the liquid metal flow to generate a sensed parameter signal;
b) comparing the sensed parameter signal with a reference signal to generate a difference signal, the reference signal being generated prior to the sensed parameter signal;
c) interpreting the difference signal to predict the presence of the undesired condition in the liquid metal outflow; and d) updating the reference signal with more recent data from the sensed parameter signal.

31. A method according to claim 30 further comprising e) repeating elements a) through d) so that the difference signal indicates changes of the sensed parameter with time.

32. A method according to claim 30 wherein elements b), c) and d) are performed by a logic unit and cyclically repeated on each cycle of the logic unit.

33. A method according to claim 30 wherein the sensed parameter comprises natural vibrations sensed by a vibration sensor physically connected with the liquid metal flow through vibration-transmissive solid structure.

34. A method according to claim 32 wherein the reference signal becomes a predicted data spectrum that can be updated on each cycle of the logic unit.

35. A method of predicting an undesired condition in a flow of liquid metal comprising the elements of:

a) obtaining time-sequenced calibration spectra of a physical wave phenomenon indicative of the flow condition;

b) calculating a predicted data spectrum of the physical wave phenomenon from the calibration spectra to indicate a flow condition at a future point in time;

c) obtaining a current data spectrum at the future point in time;

d) comparing the current data spectrum with the predicted data spectrum to provide spectral comparison data;

e) processing the spectral comparison data to provide a status signal;

f) storing the current data spectrum as the most recent entry in the sequence of calibration spectra;

g) repeating elements b) through f).

36. A method according to claim 35 wherein elements b) through f) are performed by a logic unit and cyclically repeated on each cycle of the logic unit.

37. A method according to claim 35 wherein the physical wave phenomenon comprises natural vibrations sensed by a vibration sensor physically connected with the liquid metal flow through vibration-transmissive solid structure.

38. A method according to claim 37 wherein the time sequenced calibration spectra are generated by monitoring desirable flow conditions with the vibration sensor and are stored and wherein the calibration spectra are statistically analyzed and the predicted data spectrum is generated by forward extrapolation of the calibration spectra.

39. A method according to claim 35 wherein an old calibration spectrum is removed from the calibration spectra when the current data spectrum is stored to the sequence of calibration spectra.

40. A method according to claim 35 wherein a standard deviation is applied to the predicted data spectrum to facilitate processing of the spectral comparison data.

41. A method according to claim 35 wherein the time-sequenced calibration spectra and the current data spectrum comprise multiple frequency bands and wherein each frequency band is processed by applying a standard deviation to the respective calibration frequency band and comparing the respective data frequency band to the respective calibration frequency band whereby frequency band intensities exceeding the standard deviation of the calibration spectrum indicate an undesired flow condition.

42. A method according to claim 37 wherein the vibration sensor is mechanically coupled to a teeming vessel outlet to sense vibrations in molten steel flowing through a pouring tube leading from the teeming vessel.

43. A method according to claim 35 wherein flow condition detection system is coupled with a liquid metal flow shut off valve for the valve to be operated automatically in response to a negative status signal.

* * * * *